(12) United States Patent
Hosoda et al.

(10) Patent No.: US 10,796,556 B2
(45) Date of Patent: Oct. 6, 2020

(54) INFORMATION PROCESSING SYSTEM, RECORDING MEDIUM, AND INFORMATION PROCESSING METHOD

(71) Applicant: SONY CORPORATION, Tokyo (JP)

(72) Inventors: Yasuhide Hosoda, Kanagawa (JP); Manabu Kii, Tokyo (JP); Yoshiki Takeoka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/315,910

(22) PCT Filed: Jul. 13, 2017

(86) PCT No.: PCT/JP2017/025500
§ 371 (c)(1),
(2) Date: Jan. 7, 2019

(87) PCT Pub. No.: WO2018/021040
PCT Pub. Date: Feb. 1, 2018

(65) Prior Publication Data
US 2019/0228639 A1    Jul. 25, 2019

(30) Foreign Application Priority Data
Jul. 27, 2016    (JP) ................................ 2016-147021

(51) Int. Cl.
*G08B 21/24* (2006.01)
*G06F 3/01* (2006.01)
(Continued)

(52) U.S. Cl.
CPC .............. *G08B 21/24* (2013.01); *G06F 3/01* (2013.01); *G06F 3/016* (2013.01); *G06F 9/453* (2018.02);
(Continued)

(58) Field of Classification Search
CPC ........ G08B 21/24; G16H 20/00; G06F 9/453; G06F 3/01; G06F 3/016; G06K 9/00664; G06N 5/04
(Continued)

(56) References Cited

U.S. PATENT DOCUMENTS 5,725,472 A    3/1998  Weathers
2001/0049471 A1    12/2001  Suzuki et al.
(Continued)

FOREIGN PATENT DOCUMENTS

| JP | 2001-344352 A | 12/2001 |
|----|---------------|---------|
| JP | 2009-110308 A | 5/2009 |

(Continued)

OTHER PUBLICATIONS

International Search Report and Written Opinion of PCT Application No. PCT/JP2017/025500, dated Sep. 12, 2017, 08 pages of ISRWO.
(Continued)

*Primary Examiner* — Kerri L McNally
(74) *Attorney, Agent, or Firm* — Chip Law Group

(57) ABSTRACT

The present technology relates to an information processing system, a recording medium, and an information processing method that make it possible to transmit an action suitable for a context of a user to the user in a natural way. An information processing system according to an aspect of the present technology acquires context information representing at least one of a surrounding environment of a user having a device, a feeling of the user, a situation of the user, feelings of other people around the user, or situations of the other people, recognizes a context of the user on the basis of the context information, determines an action corresponding to the context, and determines a transmission method for the action to the user, the transmission method being suitable for the context and the action. The present technology can be applied to a wearable device worn by a user.

18 Claims, 33 Drawing Sheets

(51) Int. Cl.
  *G06F 9/451* (2018.01)
  *G16H 20/00* (2018.01)
  *G06K 9/00* (2006.01)
  *G06N 5/04* (2006.01)
  *B25J 11/00* (2006.01)

(52) U.S. Cl.
  CPC ........... *G06K 9/00664* (2013.01); *G06N 5/04* (2013.01); *G16H 20/00* (2018.01); *B25J 11/00* (2013.01)

(58) Field of Classification Search
  USPC ...................................................... 340/573.1
  See application file for complete search history.

(56) References Cited

U.S. PATENT DOCUMENTS

| | | | | |
|---|---|---|---|---|
| 2002/0083025 | A1* | 6/2002 | Robarts | G06F 1/163 706/12 |
| 2013/0154826 | A1* | 6/2013 | Ratajczyk | G08B 7/06 340/539.11 |
| 2014/0129243 | A1* | 5/2014 | Utter, II | G16H 50/20 705/2 |
| 2014/0247155 | A1* | 9/2014 | Proud | H04W 4/70 340/870.16 |
| 2015/0092050 | A1* | 4/2015 | Cho | A61B 5/7405 348/143 |
| 2016/0270717 | A1* | 9/2016 | Luna | G06F 19/3481 |
| 2016/0293043 | A1 | 10/2016 | Lacroix et al. | |

FOREIGN PATENT DOCUMENTS

| | | |
|---|---|---|
| JP | 2012-160173 A | 8/2012 |
| WO | 97/22324 A1 | 6/1997 |

OTHER PUBLICATIONS

Extended European Search Report of EP Application No. 178340485, dated Jul. 17, 2019, 09 pages.

* cited by examiner

| Context ID | Condition of context | Action | Transmission method (how to transmit) |
|---|---|---|---|
| 1 | Recognize that there is piece of cake | Refrain from eating | Wind: warm wind Sound: angelic limpid voice |
| 2 | Recognize that user does not focus on class | Focus | Wind: cool wind to reduce sleepiness |
| 3 | Recognize that other person looks tough | Run away | Robot arm: pull hair |
| ... | ... | ... | ... |

FIG.8

| Context ID | Condition of context | Action | Transmission method (how to transmit) |
|---|---|---|---|
| 1 | Recognize that there is piece of cake | Refrain from eating | Wind: warm wind<br>Sound: angelic limpid voice |
| 1 | Recognize that there is piece of cake | Eat | Wind: cool wind<br>Sound: devil voice |
| 2 | Recognize that user does not focus on class | Focus | Wind: cool wind to reduce sleepiness |
| 2 | Recognize that user does not focus on class | Fall asleep | Wind: warm wind to have good sleep |
| 3 | Recognize that other person looks tough | Run away | Robot arm: pull hair |
| 3 | Recognize that other person looks tough | Stand against | Robot arm: push back |
| ... | ... | ... | ... |

FIG.12

| Context ID | Condition of context | Action | Transmission method (how to transmit) |
|---|---|---|---|
| 4 | Recognize that sender of e-mail is angry | Reply immediately | Vibration: prescribed vibration pattern<br>Sound: quavering voice |
| ... | ... | ... | ... |

FIG.15

| Context ID | Condition of context | Action | Transmission method (how to transmit) |
|---|---|---|---|
| 5 | Recognize that customer looking at product does not have willingness to buy | Serve another customer | Sound: voice of calm tone |
| 6 | Recognize that user is tired from jogging | Try a little harder | Robot arm: tap back<br>Sound: male voice of forceful tone |
| 6 | Recognize that user is tired from jogging | Rest | Robot arm: gently stroke back<br>Sound: female voice of gentle tone |
| ... | ... | ... | ... |

FIG.17

INFORMATION PROCESSING SYSTEM, RECORDING MEDIUM, AND INFORMATION PROCESSING METHOD

CROSS REFERENCE TO RELATED APPLICATIONS

This application is a U.S. National Phase of International Patent Application No. PCT/JP2017/025500 filed on Jul. 13, 2017, which claims priority benefit of Japanese Patent Application No. JP 2016-147021 filed in the Japan Patent Office on Jul. 27, 2016. Each of the above-referenced applications is hereby incorporated herein by reference in its entirety.

TECHNICAL FIELD

The present technology relates to an information processing system, a recording medium, and an information processing method, and particularly to, an information processing system, a recording medium, and an information processing method that make it possible to transmit an action suitable for a context of a user to the user in a natural way.

BACKGROUND ART

In recent years, behavior support using AI (Artificial Intelligence) has been achieved. The behavior support using the AI provides, for example, various types of information on the Internet or information to support decision-making of a person to be supported depending on a situation of the person. A function or device to perform the behavior support is also referred to as an agent.

Patent Literature 1 discloses the technology of detecting the degree of concentration of participants (presenter, audience) in a presentation, a conference, a lecture class, or the like on the basis of captured images. For example, in a case where there is audience whose degree of concentration is low, a message, e.g., "Please speak loudly." is displayed on a display in front of the presenter, and an instruction is given to the presenter.

CITATION LIST

Patent Literature

Patent Literature 1: Japanese Patent Application Laid-open No. 2012-160173

DISCLOSURE OF INVENTION

Technical Problem

The way to provide the information to support decision-making becomes a problem in some cases.

For example, in a case where information is provided by displaying a message as described in Patent Literature 1 or by displaying a picture, a person to be supported has to be at a position where the person can see it. Further, in a case where information is provided by using sound, the person may not want people around the person to hear it.

The present technology has been made in view of such circumstances and makes it possible to transmit an action suitable for a context of a user to the user in a natural way.

Solution to Problem

An information processing system of an aspect of the present technology includes: an acquisition unit that acquires context information representing at least one of a surrounding environment of a user having a device, a feeling of the user, a situation of the user, feelings of other people around the user, or situations of the other people; and a controller that recognizes a context of the user on a basis of the context information, determines an action corresponding to the context, and determines a transmission method for the action to the user, the transmission method being suitable for the context and the action.

In the aspect of the present technology, context information representing at least one of a surrounding environment of a user having a device, a feeling of the user, a situation of the user, feelings of other people around the user, or situations of the other people is acquired, and a context of the user is recognized on a basis of the context information. Further, an action corresponding to the context is determined, and a transmission method for the action to the user is determined, the transmission method being suitable for the context and the action.

Advantageous Effects of Invention

According to the present technology, it is possible to transmit an action suitable for a context of a user to the user in a natural way.

It should be noted that the effects described herein are not necessarily limited and any of the effects described herein may be produced.

BRIEF DESCRIPTION OF DRAWINGS

FIG. 8 is a diagram showing an example of action information.

FIG. 12 is a diagram showing another example of the action information.

FIG. 15 is a diagram showing an example of the action information.

FIG. 17 is a diagram showing an example of the action information.

MODE(S) FOR CARRYING OUT THE INVENTION

Detailed Description

Hereinafter, modes for carrying out the present technology will be described. Description will be given in the following order.

Natural Transmission Method
First Embodiment Transmission of Action Suitable for Context
Second Embodiment Transmission of Two Opposite Actions
Third Embodiment Transmission of Action Opposite to User's Behavior
Fourth Embodiment Method of Determining Action To Be Transmitted

MODIFIED EXAMPLES

<<Natural Transmission Method>>

Figure 1:
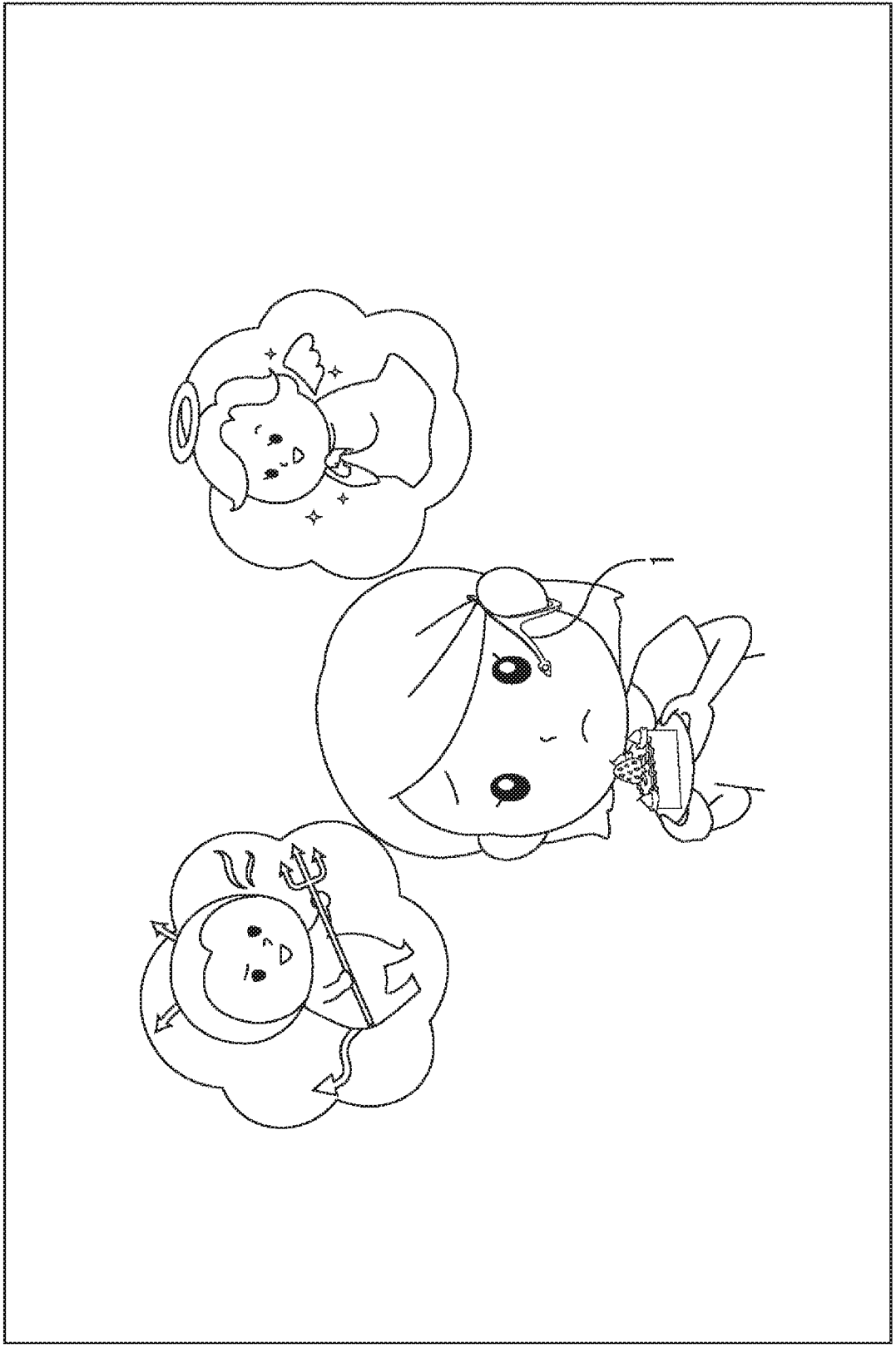
FIG. 1 is a view showing a situation of behavior support using a wearable device according to one embodiment of the present technology.

FIG. 1 is a view showing a situation of behavior support using a wearable device according to one embodiment of the present technology.

The wearable device 1 wearable on an ear of a user is an agent device that performs behavior support for a user as a wearer. The behavior support by the wearable device 1 is performed so as to detect a context of the user and transmit an action corresponding to the context by a method suitable for the context and the content of the action.

Here, the context of the user includes at least one of the surrounding environment of the user wearing the wearable device 1, the feeling of the user, the situation of the user, the feelings of other people around the user, or the situations of the other people around the user. The wearable device 1 has a function of generating information to be used for detecting a surrounding environment or the like by using a mounted camera or various sensors.

Transmission of an action by the wearable device 1 is performed by a method using wind, a method using vibration, or a method using sound such that people around the user is not aware of it.

For example, the transmission of an action by using wind is performed so as to blow wind having a temperature corresponding to an action to be transmitted, to the vicinity of the user's face or the like. Further, the transmission of an action by using vibration is performed so as to generate vibration having a pattern corresponding to an action to be transmitted. The transmission of an action by using sound is performed so as to output sound having a tone corresponding to an action to be transmitted, at low volume, from a speaker provided in the vicinity of the ear.

The wearable device 1 also has a function of sending wind of different temperatures, a function of vibrating in different patterns, and a function of outputting sound of different tones from the speaker near the ear.

In such a manner, the wearable device 1 transmits an action suitable for the context to the user in a natural way, to thus perform behavior support. A natural transmission method means a transmission method performed such that people around the user do not notice the transmission of an action.

For example, in a case where an action is transmitted by displaying a message, this makes the user to be conscious of viewing the message. Depending on circumstances, the user does not want people around the user to know that the user is viewing the message.

Further, in a case where an action is transmitted by using sound at high volume in a quiet space or in a case where an action is transmitted in a situation where another person exists and in such a manner that the other person may notice the transmission of an action, the user may feel awkward.

Transmitting an action by a natural method such that people around the user do not notice it can also be a so-called thoughtful transmission way.

Further, the transmission of an action by the wearable device 1 is performed by appropriately transmitting two opposite actions.

For example, as shown in FIG. 1, in a case where there is a piece of cake in front of a user on a diet, two actions, i.e., an action of "refrain" and an action of "eat", are transmitted. The former action is an action based on a goal, which is a diet, and the latter action is an action being against the goal. Those actions can be actions having opposite content.

The illustration of an angel shown in FIG. 1 represents an image to encourage the achievement of the goal by transmitting an action of "refrain". Meanwhile, the illustration of a devil represents an image to tempt the user to do an action contrary to the achievement of the goal by transmitting an action of "eat".

It should be noted that the fact that a diet is the goal is set by the user as a situation of the user, for example. Further, the fact that there is a piece of cake in front of the user is identified by, for example, analyzing an image captured by a camera of the wearable device 1.

In such a manner, the wearable device 1 is capable of transmitting two opposite actions as actions suitable for the context of the user.

For example, it is thought that even if a user has a strong will to take one of actions, the user potentially has a willingness to take an action contrary to the one action. Presenting an action following such a potential willingness and giving the user a push can be a thoughtful transmission way.

Further, a user having a stronger will is less willing to take an action that goes against his/her will. Thus, when such a user having a strong will to take one of the actions is caused to take another action contrary to the one action, the user may discover something new. Even in the sense that an action leading to a discovery of something new is presented as an option, transmitting two opposite actions can be a thoughtful transmission way.

Operations of respective devices that transmit the above-mentioned actions suitable for the context of the user in a thoughtful transmission way will be described later with reference to flowcharts.

First Embodiment Transmission of Action Suitable for Context

<1. Configuration Example of Information Processing System>

Figure 2:
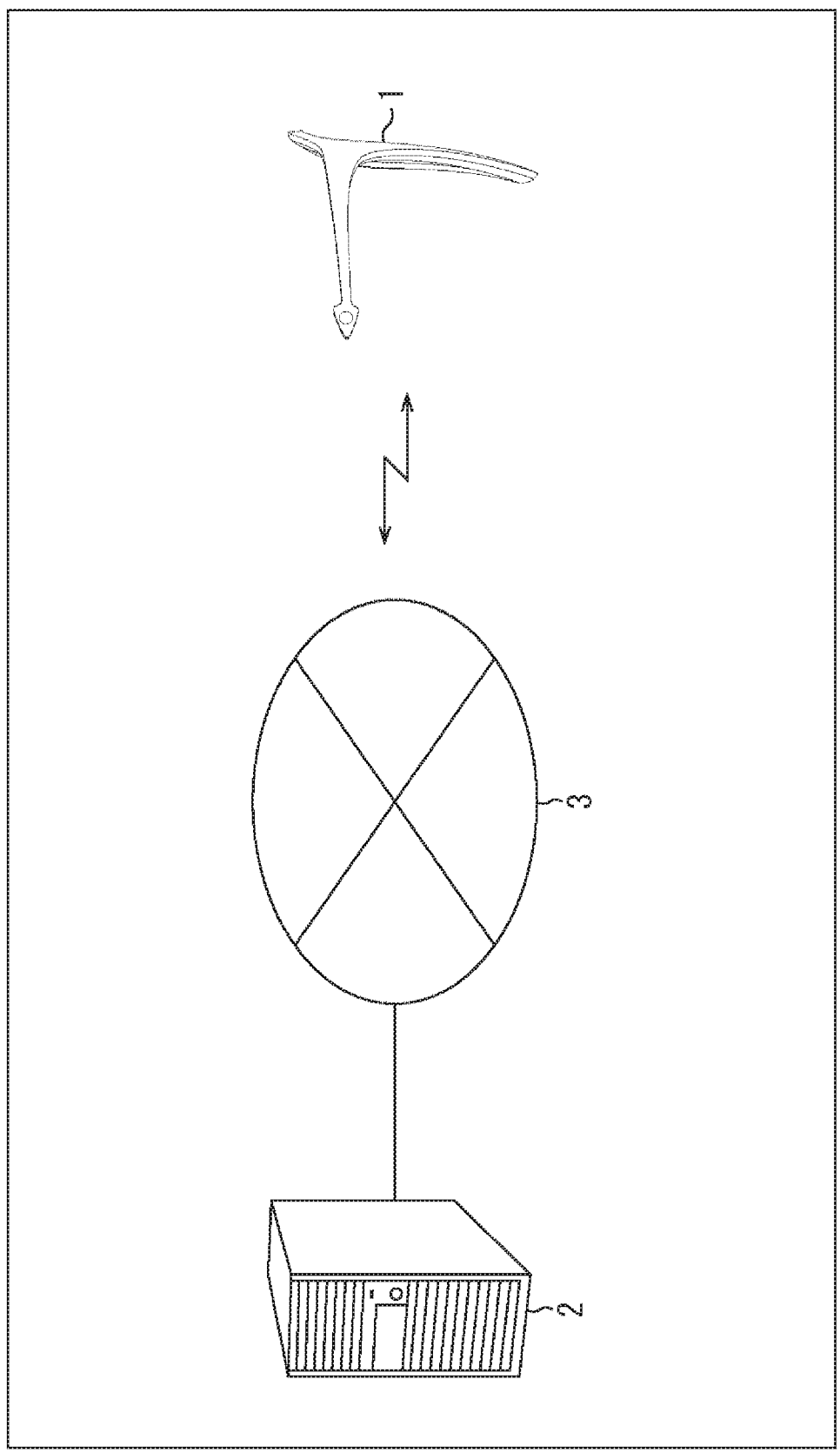
FIG. 2 is a view showing a configuration example of an information processing system.

FIG. 2 is a view showing a configuration example of an information processing system.

The information processing system of FIG. 2 is configured by connecting the wearable device 1 and a control server 2 to each other via a network 3 such as the Internet.

The wearable device 1 generates images captured by cameras and sensor data detected by various sensors as context information to be used for recognizing a context of the user, and sends the context information to the control server 2.

Further, the wearable device 1 receives a control signal sent from the control server 2 in response to the sending of the context information. The control signal is information representing at least the content of an action to be transmitted to the user and a transmission method for the action. The wearable device 1 transmits an action determined by the control server 2 to the user by a method determined by the control server 2 according to the control signal.

The control server 2 receives the context information sent from the wearable device 1 and recognizes the context of the user on the basis of the context information. Further, the control server 2 determines an action corresponding to the recognized context and also determines a transmission method for an action.

In the control server 2, a database in which an action and a transmission method are registered in association with each context is managed. The control server 2 sends the control signal, which represents the content of the determined action and the transmission method suitable for the context and the action, to the wearable device 1 to thus control transmission of the action to the user.

As will be described later, an information processing system to which the present technology is applied can be achieved by a single wearable device 1. A plurality of wearable devices similar to the wearable device 1 may be connected to the network 3.

<1-1. Configuration Example of Wearable Device 1>

Figure 3:
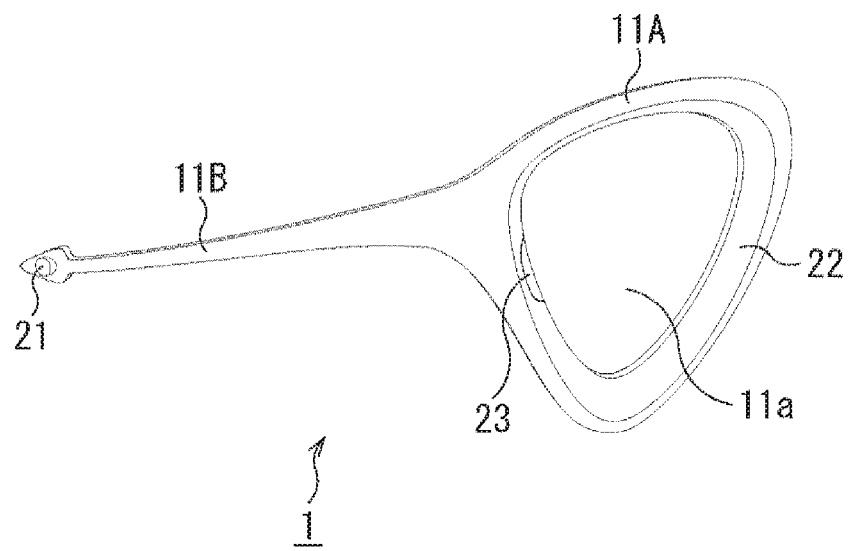
FIG. 3 is a view showing an example of an outer appearance of the wearable device.
Figure 4:
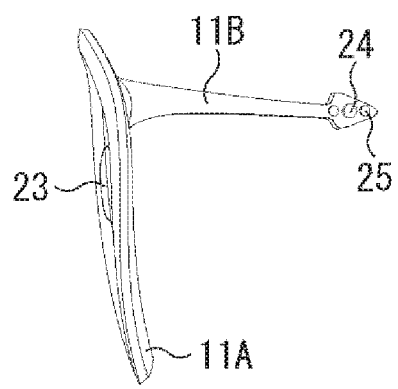
FIG. 4 is a view showing an example of the outer appearance of the wearable device.

FIGS. 3 and 4 are views each showing an example of an outer appearance of the wearable device 1.

The casing of the wearable device 1 is configured by an ear hook portion 11A and an arm portion 11B that are integrally formed, the ear hook portion 11A having an inverted triangular shape with the gently rounded corners, the arm portion 11B having an arrow shape whose width is gradually narrowed from the base toward the tip.

The ear hook portion 11A has an opening 11a having substantially the same shape as that of the ear hook portion 11A. The wearable device 1 is worn by passing the left ear through the opening 11a. In FIG. 3, the left side corresponds to the front side of the face of the user, and the right side corresponds to the back side of the head. The surface shown in FIG. 3 is the outer surface of the casing, and the rear surface is the inner surface of the casing.

An edge portion 22 surrounding the opening 11a is made of a flexible material such as a low resilient urethane material. The edge portion 22 softens by body temperature, so that the shape and size of the opening 11a can be appropriately deformed. The edge portion 22 is deformed, and thus the opening 11a is widened to adapt to the ear or caught to fit the ear.

The edge portion 22 may be made of a shape-memory alloy that is deformed into a predetermined shape by body temperature. The entire ear hook portion 11A can also be made of a low resilient urethane material or a shape-memory alloy.

A speaker 23 is provided at a position near the front of the edge portion 22. When the wearable device 1 is worn, the speaker 23 is positioned near the cavity of the ear.

The arm portion 11B is formed to be gently curved toward the inside of the wearable device 1. When the wearable device 1 is worn, the tip of the arm portion 11B is positioned near the left eye of the user. A front imaging camera 21 as a camera for imaging the front is provided outside a V-shaped portion at the tip of the arm portion 11B (FIG. 3). A line-of-sight detection camera 24 as a camera for detecting the line of sight, and a projection unit 25 are provided inside the V-shaped portion at the tip of the arm portion 11B (FIG. 4).

For example, when an image captured by the line-of-sight detection camera 24 is analyzed, a motion of the line of sight is detected. Further, a region being viewed by the user in an image captured by the front imaging camera 21 is identified on the basis of a direction of the detected line of sight.

The projection unit 25 is a retina-direct-projection display module. The projection unit 25 projects an image on the retina of the left eye of the user to present information.

Figure 5:
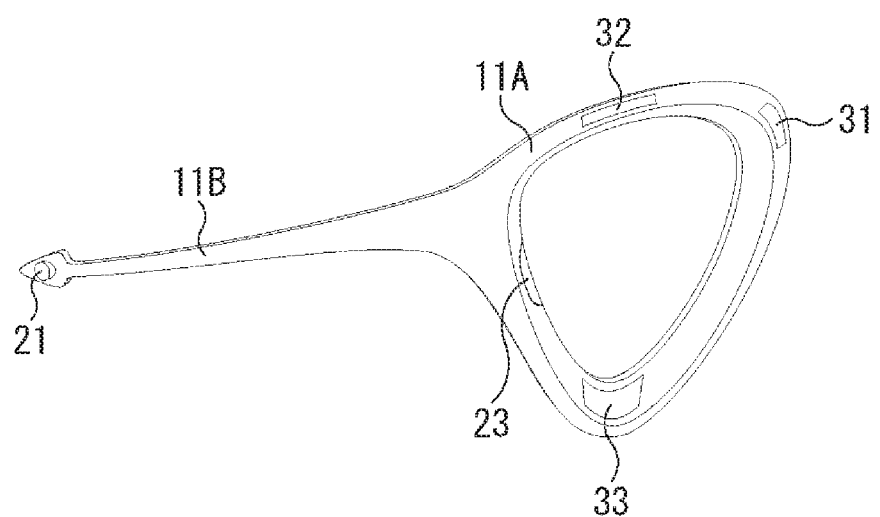
FIG. 5 is a view showing another example of the outer appearance of the wearable device.

FIG. 5 is a view showing another example of the outer appearance of the wearable device 1.

In the example of FIG. 5, an attachment portion 31 is provided at a position near the rear side of the ear hook portion 11A. A small robot arm is attachable to the attachment portion 31. The robot arm attached to the attachment portion 31 is used for transmitting an action.

In other words, transmission of an action by the wearable device 1 is also performed by a method using the drive of the robot arm. The robot arm is attached such that the tip thereof pinches the hair or a part of the ear of the user. The wearable device 1 performs operations such as pulling the hair and pulling the ear by using the robot arm and transmits an action to the user.

The tip of the robot arm may be caused to reach the neck or back of the user and push it, thus transmitting an action. The robot arm is disclosed in, for example, Japanese Patent Application Laid-open No. 2002-6924.

An outlet 32 is provided at a position near the upper side of the ear hook portion 11A. An action is transmitted as described above by using wind to be discharged from the outlet 32. A mechanism to blow wind having different temperatures is disclosed in, for example, Japanese Patent Application Laid-open No. 2006-136628. An action may be transmitted by using wind with the amount corresponding to an action to be transmitted.

An operation unit 33 is provided at a position near the lower side of the ear hook portion 11A. The operation unit 33 is, for example, a touch sensor and detects an operation of the user. When the wearable device 1 is worn, the operation unit 33 is positioned near the ear lobe. The user can perform various operations by a motion such as a touch to the ear lobe. A motion of the user to touch the ear lobe may be detected with a camera, an infrared ray sensor, or the like, so that the operation can be performed.

The positions of the attachment portion 31, the outlet 32, and the operation unit 33 shown in FIG. 5 can be changed to any positions. Hereinafter, description will be given assuming that the wearable device 1 has the configuration shown in FIG. 5. A robot arm is attached to the attachment portion 31.

Figure 6:
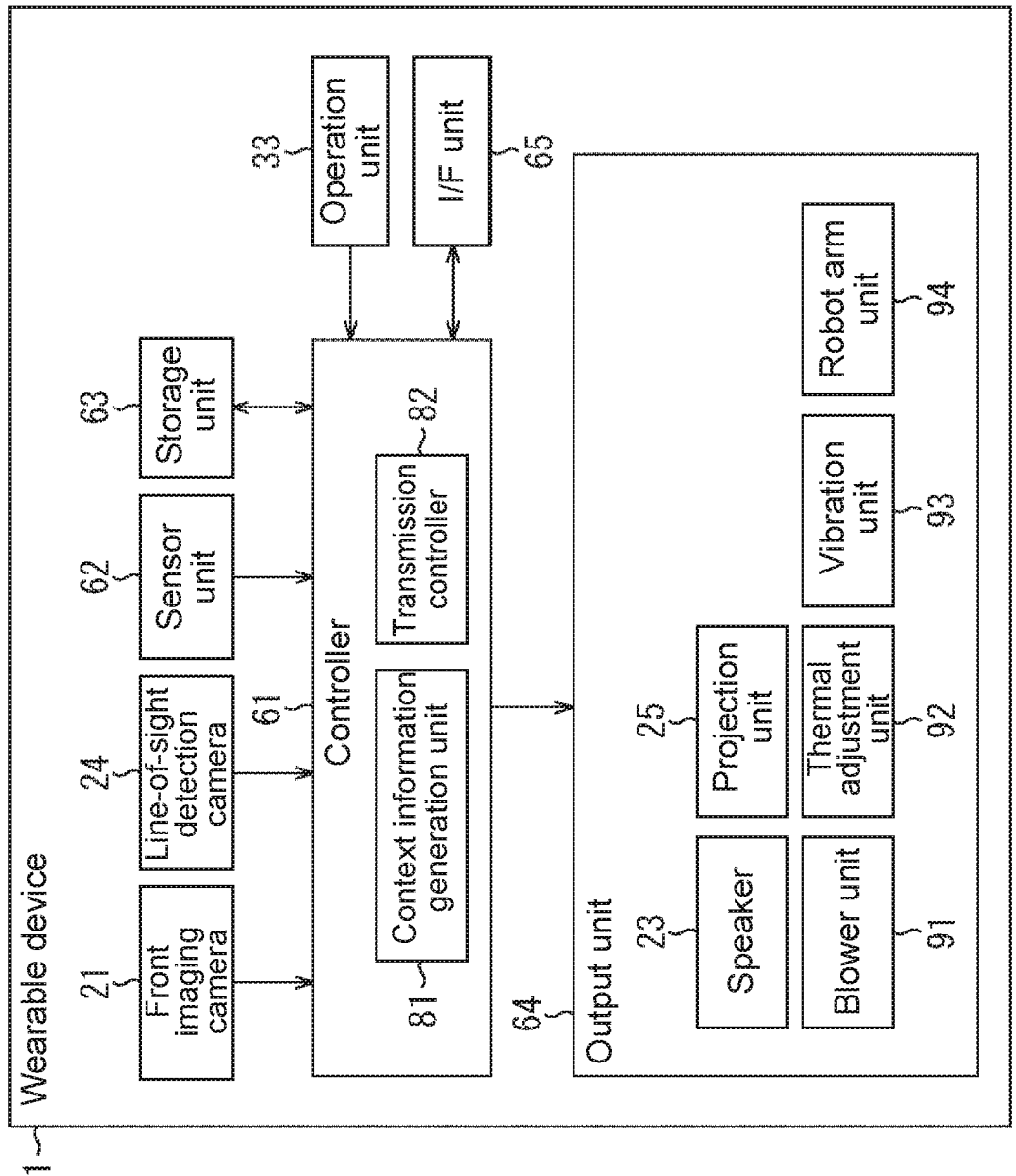
FIG. 6 is a block diagram showing a configuration example of the wearable device.

FIG. 6 is a block diagram showing a configuration example of the wearable device 1.

The wearable device 1 is configured by connecting the front imaging camera 21, the line-of-sight detection camera 24, the operation unit 33, a sensor unit 62, a storage unit 63, an output unit 64, and an I/F unit 65 to a controller 61.

The controller 61 includes a CPU, a ROM, a RAM, and the like. The controller 61 executes a predetermined program by the CPU and controls the whole operations of the wearable device 1.

The front imaging camera 21 images the front of the user wearing the wearable device 1 and outputs an image obtained by imaging to the controller 61. The image captured by the front imaging camera 21 may be a still image or a moving image.

The line-of-sight detection camera 24 images a range including the left eye of the user wearing the wearable device 1 and outputs an image obtained by imaging to the controller 61.

The operation unit 33 detects an operation of the user and outputs a signal indicating the content of the operation to the controller 61. The operation unit 33 may be configured by not only a touch sensor provided in the vicinity of the ear lobe of the user but also a touch sensor or a button provided at another position.

The sensor unit 62 is configured by various sensors such as an acceleration sensor, a gyroscope sensor, a GPS sensor, and a biosensor. The biosensor configuring the sensor unit 62 includes a body temperature sensor, a heart rate sensor, and the like. The biosensor may include a sensor that detects brain waves such as alpha waves and beta waves. For example, the degree of concentration or the like of the user is detected from a measured value measured by the biosensor. The sensor unit 62 outputs sensor data indicating measured values measured by the respective sensors to the controller 61.

The storage unit 63 is configured by a flash memory or the like. The storage unit 63 stores various types of data.

The output unit 64 includes the speaker 23, the projection unit 25, a blower unit 91, a thermal adjustment unit 92, a vibration unit 93, and a robot arm unit 94.

The speaker 23 outputs sound or sound effects.

The projection unit 25 applies light and projects an image onto the retina of the eye of the user.

The blower unit 91 is configured by a small fan or the like and sends wind from the outlet 32.

The thermal adjustment unit 92 is configured by a small module to be a heat generation source and a cooling module. The heat generated by the thermal adjustment unit 92 and the temperature of wind sent from the blower unit 91 by a cooling function of the thermal adjustment unit 92 are adjusted.

The vibration unit 93 generates vibration.

The robot arm unit 94 is a robot arm attached to the attachment portion 31. The robot arm unit 94 performs various operations under the control of the controller 61.

The I/F unit 65 are an interface for near field communication such as Bluetooth (registered trademark) or a wireless LAN, and an interface for wireless communication using a mobile communication system (WAN) such as 3G or 4G. The I/F unit 65 performs communication with an external device such as the control server 2.

In the wearable device 1 having the above-mentioned configuration, the CPU of the controller 61 executes a predetermined program, and thus a context information generation unit 81 and a transmission controller 82 are achieved.

The context information generation unit 81 acquires a front image captured by the front imaging camera 21, an image captured by the line-of-sight detection camera 24, and sensor data supplied from the sensor unit 62 and generates context information.

As described above, the context includes at least one of the surrounding environment of the user wearing the wearable device 1, the feeling of the user, the situation of the user, the feelings of other people around the user, or the situations of the other people around the user.

For example, the context information generation unit 81 analyzes the image captured by the line-of-sight detection camera 24 to detect the line of sight of the user, and identifies a region viewed by the user in the entire front image. The context information generation unit 81 generates context information including the front image, the information of the region viewed by the user, and the sensor data.

The front image and the information of the region viewed by the user are information that can be used for identifying the surrounding environment of the user, the situation of the user, the feelings of other people around the user, and the situations of the other people around the user.

For example, when the front image is analyzed, the surrounding environment of the user, e.g., "the user stays outside", can be identified.

Further, when an image of a person within the region viewed by the user among people shown in the front image is analyzed, the situation of the user, e.g., "the user is talking with another person", can be identified.

When the front image is analyzed, the feelings of the other people, e.g., "people around the user are delighted", or the situations of the other people, e.g., "people around the user are running", can be identified.

Meanwhile, the sensor data supplied from the sensor unit 62 is information that can be used for identifying the feeling of the user wearing the wearable device 1 and the situation of the user.

For example, the feeling of the user, e.g., "the user is angry", can be identified from the brain waves.

Further, the situation of the user, e.g., "the user is walking" or "the user is jogging", can be identified from a body temperature, a heart rate, or vibration (acceleration, angular velocity).

In such a manner, the context information generated by the context information generation unit 81 is information used for recognizing the surrounding environment of the user, the feeling of the user, the situation of the user, the feelings of other people around the user, and the situations of the other people around the user. The context information generation unit 81 controls the I/F unit 65 to send the generated the context information to the control server 2.

The transmission controller 82 controls the I/F unit 65 to receive a control signal sent from the control server 2. The transmission controller 82 controls each block of the output unit 64 according to the control signal and transmits an action determined by the control server 2 to the user by a transmission method determined by the control server 2.

<1-2. Configuration Example of Control Server 2>

Figure 7:
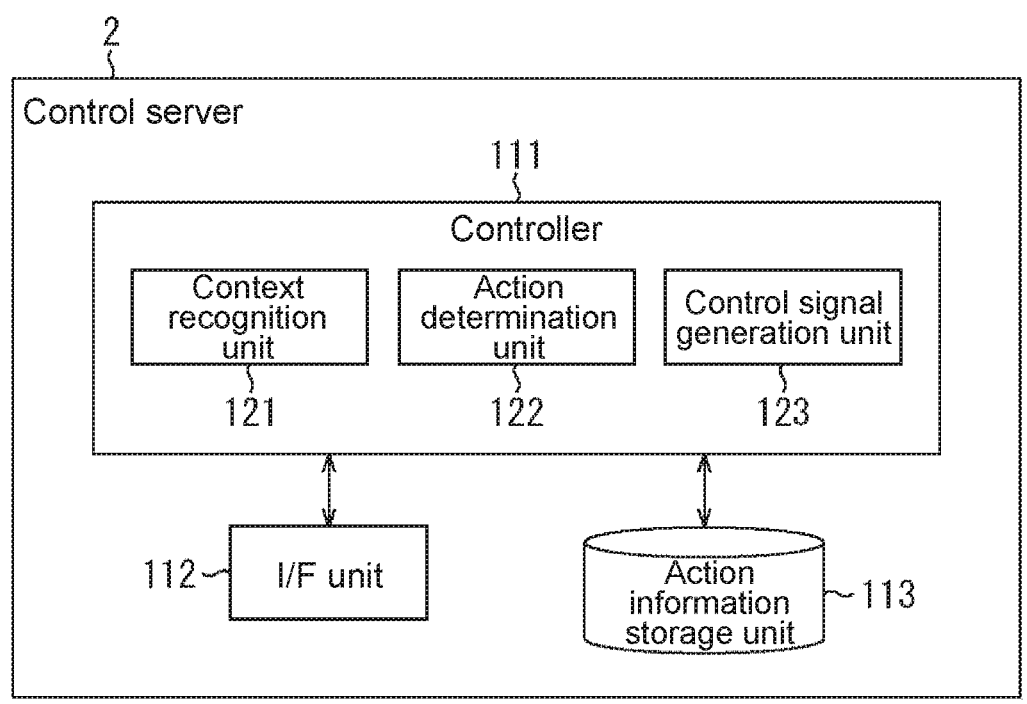
FIG. 7 is a block diagram showing a configuration example of a control server.

FIG. 7 is a block diagram showing a configuration example of the control server 2.

The control server 2 is configured by connecting an I/F unit 112 and an action information storage unit 113 to a controller 111.

The controller 111 includes a CPU, a ROM, a RAM, and the like. The controller 111 executes a predetermined program by the CPU and controls the whole operations of the control server 2.

The I/F unit 112 is an interface that performs wireless or wired communication. The I/F unit 112 performs communication with the wearable device 1 via the network 3.

The action information storage unit 113 is configured by an HDD or an SSD. The action information storage unit 113 stores action information. The action information indicates a correspondence relationship between a context, an action corresponding to the context, and a transmission method suitable for the context and the action. The action information storage unit 113 configures a database of the action information.

In the control server 2, the CPU of the controller 111 executes a predetermined program, and thus a context recognition unit 121, an action determination unit 122, and a control signal generation unit 123 are achieved.

The context recognition unit 121 controls the I/F unit 112 to acquire context information sent from the wearable device 1. Further, the context recognition unit 121 recognizes the context of the user on the basis of the acquired context information. The context recognition unit 121 has information for recognizing the context, such as data for recognizing an object appearing in an image or data for detecting a pattern of sensor data.

The action determination unit 122 refers to an action database managed by the action information storage unit 113 to determine an action corresponding to the context recognized by the context recognition unit 121 and a transmission method therefor.

The control signal generation unit 123 generates a control signal indicating the action and the transmission method determined by the action determination unit 122. The control signal generation unit 123 controls the I/F unit 112 to send the control signal to the wearable device 1.

FIG. 8 is a diagram showing an example of action information.

The example of FIG. 8 shows action information regarding three contexts of context IDs 1, 2, and 3.

The context of the context ID 1 is a context selected under the condition that it is recognized that there is a piece of cake.

It is recognized that there is a piece of cake, for example, when a piece of cake appears in a region viewed by the user in the front image included in the context information. The fact that there is a piece of cake is, for example, a recognition result of the surrounding environment of the user.

When it is recognized that there is a piece of cake, "refrain from eating" is determined as an action to be transmitted to the user. Further, a method of blowing warm wind and using sound of an angelic limpid tone is determined as a transmission method for "refrain from eating".

The context of the context ID 2 is a context selected under the condition that it is recognized that the user does not focus on the class.

It is recognized that the user is in class, for example, when the front image included in the context information is analyzed and a feature representing that the user is in class is detected. Further, it is recognized that the user does not focus on the class, for example, when the sensor data included in the context information shows a measured value that appears when the user does not focus. The fact that the user does not focus on the class is, for example, a recognition result of the surrounding environment of the user and the situation of the user.

When it is recognized that the user does not focus on the class, "focus" is determined as an action to be transmitted to the user. Further, a method of blowing cool wind to reduce sleepiness is determined as a transmission method for "focus".

The context of the context ID 3 is a context selected under the condition that it is recognized that the other person looks tough.

It is recognized that there is other person, for example, when the front image included in the context information is analyzed and a feature representing that the user is talking with other person is detected. Further, it is recognized that the other person looks tough on the basis of, for example, the height of a person appearing in the region viewed by the user or the size of the arm of the person. The fact that the other person looks tough is, for example, a recognition result of the surrounding environment of the user and the situations of other people around the user.

When it is recognized that the other person looks tough, "run away" is determined as an action to be transmitted to the user. Further, a method of pulling the hair with the robot arm unit 94 is determined as a transmission method for "run away".

In the action database of FIG. 8, a single action and a single transmission method are managed in association with a single context. In the example of FIG. 8, three pieces of action information are shown, but more pieces of action information are registered in the action database.

<3. Operation of Information Processing System>

Here, an operation of the information processing system of FIG. 2 will be described. As shown in FIG. 8, it is assumed that a single action and a single transmission method are managed in association with a single context.

First, the sending processing of the wearable device 1 will be described with reference to a flowchart of FIG. 9.

Figure 9:
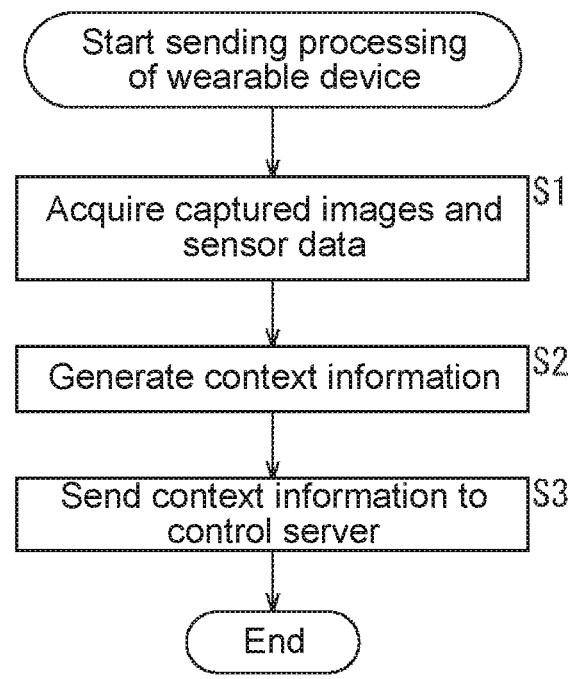
FIG. 9 is a flowchart for describing sending processing of the wearable device.

The processing of FIG. 9 is performed when the user is wearing the wearable device 1. It is assumed that the user performs daily activities such as walking around the city and going to school while wearing the wearable device 1. During those activities, the imaging by the front imaging camera 21 and the line-of-sight detection camera 24 and the measurement by the sensor unit 62 are repetitively performed.

In Step S1, the context information generation unit 81 acquires a front image captured by the front imaging camera 21, an image captured by the line-of-sight detection camera 24, and sensor data supplied from the sensor unit 62.

In Step S2, the context information generation unit 81 generates context information on the basis of the captured images and the sensor data.

In Step S3, the context information generation unit 81 sends the generated context information to the control server 2 and terminates the processing. The above-mentioned processing is repetitively performed at predetermined periods.

Next, the control processing of the control server 2 will be described with reference to a flowchart of FIG. 10.

Figure 10:
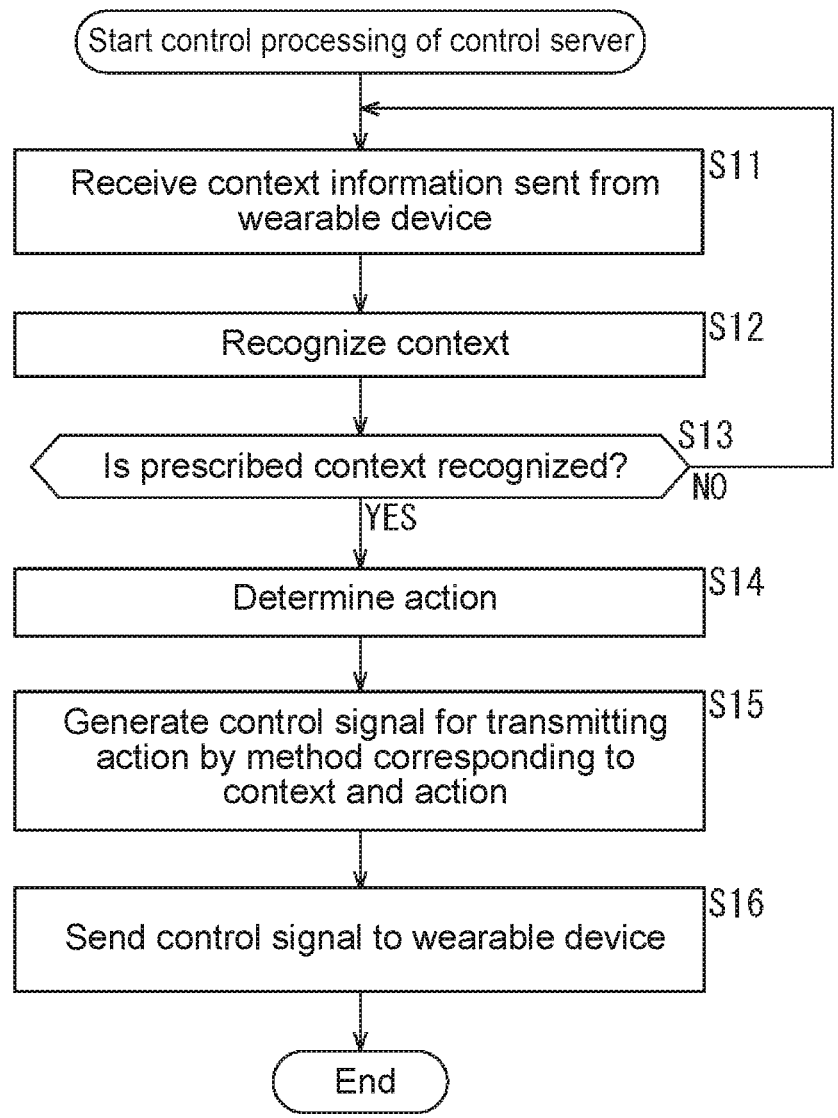
FIG. 10 is a flowchart for describing control processing of the control server.

The processing of FIG. 10 is started when the processing of FIG. 9 is performed by the wearable device 1 and the context information is sent from the wearable device 1.

In Step S11, the context recognition unit 121 receives and acquires the context information sent from the wearable device 1.

In Step S12, the context recognition unit 121 recognizes the context on the basis of the acquired context information.

In Step S13, the context recognition unit 121 determines whether a prescribed context registered in the action database is recognized or not.

When the context recognition unit 121 determines in Step S13 that a prescribed context is not recognized, the processing returns to Step S11 and the following processing is repeated. Meanwhile, when the context recognition unit 121 determines in Step S13 that a prescribed context is recognized, the processing proceeds to Step S14.

In Step S14, the action determination unit 122 refers to the action database managed by the action information storage unit 113 and determines an action corresponding to the context recognized by the context recognition unit 121.

In Step S15, the control signal generation unit 123 generates a control signal that indicates the action and transmission method determined by the action determination unit 122. The transmission method determined by the action determination unit 122 is a method managed in the action database as a method suitable for the context and the action corresponding thereto.

In Step S16, the control signal generation unit 123 sends the control signal to the wearable device 1 and terminates the processing.

Next, the action transmission processing of the wearable device 1 will be described with reference to a flowchart of FIG. 11.

Figure 11:
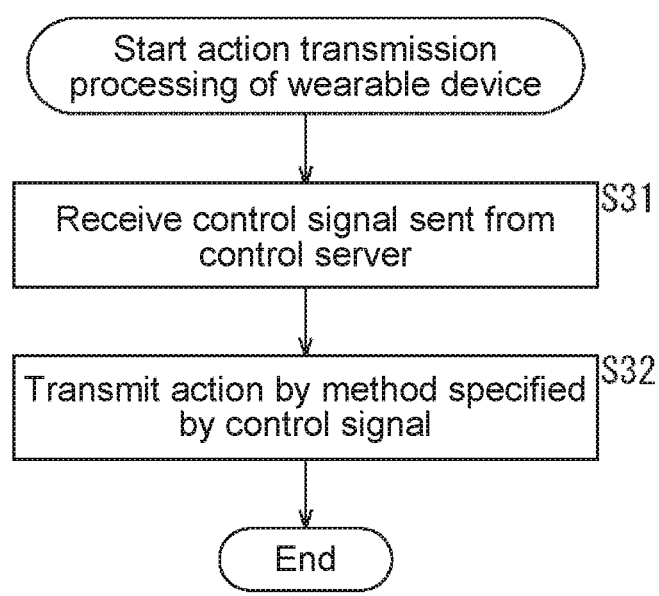
FIG. 11 is a flowchart for describing action transmission processing of the wearable device.

The processing of FIG. 11 is started when the processing of FIG. 10 is performed by the control server 2 and a control signal is sent from the control server 2.

In Step S31, the transmission controller 82 receives and acquires the control signal sent from the control server 2.

In Step S32, the transmission controller 82 controls each unit of the output unit 64 according to the control signal, to transmit an action determined by the control server 2 to the user by a transmission method determined by the control server 2, and terminates the processing.

The series of processing described above allows an action corresponding to the context of the user to be transmitted in a natural way such that people around the user do not notice it.

For example, when the context of "there is a piece of cake" is recognized, "refrain from eating" is determined as an action corresponding to the context in the control server 2. Further, a transmission method suitable for the context of "there is a piece of cake" and an action of "refrain from eating", a method of blowing warm wind and using sound of an angelic limpid tone is determined. The control server 2 sends a control signal indicating the content described above to the wearable device 1.

In the wearable device 1, the blower unit 91 and the thermal adjustment unit 92 are controlled to blow warm wind to the use's face or the like according to the control signal. Further, the speaker 23 is controlled to output sound of an angelic limpid tone, e.g., "Don't eat it.", to the ear.

For example, when the user finds a shelf on which pieces of cake are put during shopping in a supermarket, an action of "refrain from eating" is to be transmitted to the user in such a manner that people around the user do not notice it.

If the sound, e.g., "Don't eat it.", is output such that people around the user hear it in order to transmit an action of "refrain from eating", the people around the user may know that the user is on a diet and the user may feel awkward. In such a manner, transmitting an action in a natural way can prevent the user from feeling awkward.

Transmitting an action of "refrain from eating" without causing the user to feel awkward can be a thoughtful transmission way.

Second Embodiment Transmission of Two Opposite Actions

As described with reference to FIG. 1, a case where two opposite actions are transmitted will be described. Description overlapping with the above-mentioned description will be omitted appropriately.

FIG. 12 is a diagram showing another example of the action information.

In the example of FIG. 12, two actions and transmission methods are managed in association with each of three contexts of the context IDs 1, 2, and 3.

Two actions of "refrain from eating" and "eat" are associated with the context of the context ID 1 to be selected under the condition that it is recognized that there is a piece of cake. When it is recognized that there is a piece of cake, two opposite actions of "refrain from eating" and "eat" are determined as actions to be transmitted to the user.

Further, a method of blowing warm wind and using sound of an angelic limpid tone is determined as a transmission method for "refrain from eating". Meanwhile, a method of blowing cool wind and using sound of a devil tone is determined as a transmission method for "eat". A difference in tone is expressed by using, for example, the frequency of voice, rhythm, enunciation, a difference in gender of a speaker (man/woman), and the like.

Two actions of "focus" and "fall asleep" are associated with the context of the context ID 2 to be selected under the condition that it is recognized that the user does not focus on the class. When it is recognized that the user does not focus on the class, two opposite actions of "focus" and "fall asleep" are determined as actions to be transmitted to the user.

Further, a method of blowing cool wind to reduce sleepiness is determined as a transmission method for "focus". Meanwhile, a method of blowing warm wind is determined as a transmission method for "fall asleep".

Two actions of "run away" and "stand against" are associated with the context of the context ID 3 to be selected under the condition that it is recognized that the other person looks tough. When it is recognized that the other person looks tough, two opposite actions of "run away" and "stand against" are determined as actions to be transmitted to the user.

Further, a method of pulling the hair of the user with the robot arm unit 94 is determined as a transmission method for "run away". Meanwhile, a method of pushing the back of the user with the robot arm unit 94 is determined as a transmission method for "stand against".

In such a manner, in the control server 2, the two actions and the respective actions are managed in association with the single context. Three or more actions and transmission methods for the respective actions may be managed in association with the single context.

For example, the transmission method for "refrain from eating", i.e., the method of blowing warm wind and using sound of an angelic limpid tone, expresses encouragement for the action that suits a goal or a diet, and is a method suitable for the action. Further, the transmission method for "eat", i.e., the method of blowing cool wind and using sound of a devil tone, expresses temptation for the action that goes against the goal, and is a method suitable for the action.

Since those actions are determined according to the respective contexts, each of the transmission methods managed in the action database is a method suitable for a context and an action corresponding to the context.

Next, the control processing of the control server 2 will be described with reference to a flowchart of FIG. 13.

Figure 13:
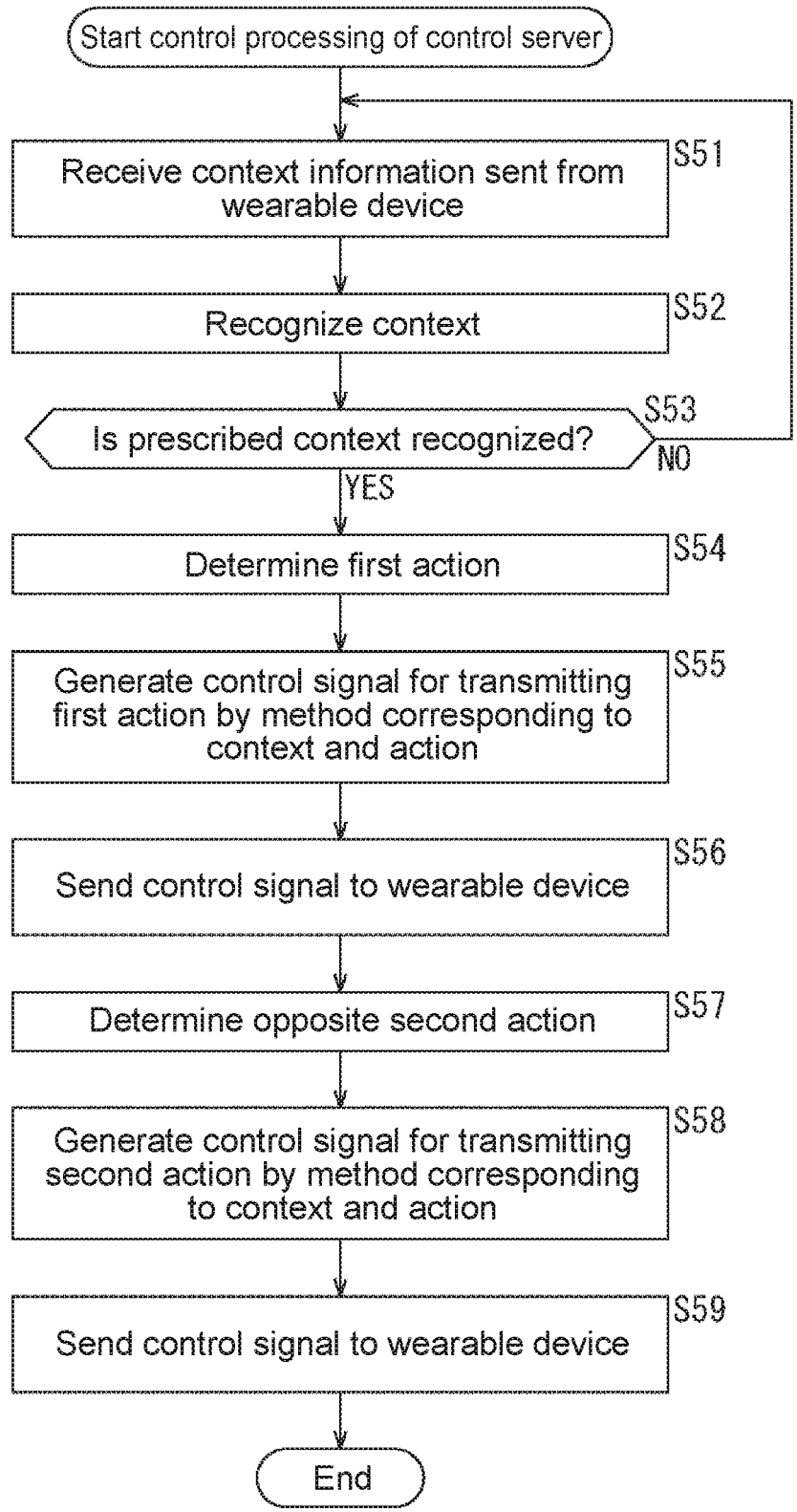
FIG. 13 is a flowchart for describing control processing of a control server according to a second embodiment.

The processing of FIG. 13 is started when the processing of FIG. 9 is performed by the wearable device 1 and the context information is sent from the wearable device 1.

In Step S51, the context recognition unit 121 receives and acquires the context information sent from the wearable device 1.

In Step S52, the context recognition unit 121 recognizes the context on the basis of the acquired context information.

In Step S53, the context recognition unit 121 determines whether a prescribed context registered in the action database is recognized or not. When the context recognition unit 121 determines in Step S53 that a prescribed context is recognized, the processing proceeds to Step S54.

In Step S54, the action determination unit 122 refers to the action database managed by the action information storage unit 113 and determines a first action corresponding to the context recognized by the context recognition unit 121 and a transmission method therefor. Of the two opposite actions, one of the actions and a transmission method therefor are determined.

In Step S55, the control signal generation unit 123 generates a control signal indicating the first action and the transmission method that are determined by the action determination unit 122.

In Step S56, the control signal generation unit 123 sends the control signal to the wearable device 1.

In Step S57, the action determination unit 122 determines a second action corresponding to the context recognized by the context recognition unit 121 and a transmission method therefor. Of the two opposite actions, the other action and a transmission method therefor are determined.

In Step S58, the control signal generation unit 123 generates a control signal indicating the second action and the transmission method that are determined by the action determination unit 122.

In Step S59, the control signal generation unit 123 sends the control signal to the wearable device 1.

The wearable device 1 that has received the control signals sent in Step S56 and Step S59 performs, at respective timings, processing similar to the processing described with reference to FIG. 11, and transmits each of the two opposite actions to the user.

This achieves a thoughtful transmission way in which two opposite actions are transmitted in a natural way.

In the example of FIG. 13, the wearable device 1 is notified of the two actions by using the control signals different from each other, but the wearable device 1 is notified of the two actions collectively by a single control signal.

Further, in a case where the two actions are managed in association with a single context, one of the actions may be transmitted.

Third Embodiment Transmission of Action Opposite to User's Behavior

In a case where the two actions are managed in association with a single context, an action opposite to the action that the user tries to take may be transmitted.

For example, the two actions of "refrain from eating" and "eat" are managed for the context of "there is a piece of cake". However, when it is predicted that the user refrains from eating the piece of cake, the action of "eat" is transmitted.

Meanwhile, when it is predicted that the user tries to eat the piece of cake, the action of "refrain from eating" is transmitted. What behavior to be taken by the user for the current context is predicted by monitoring before transmitting an action, and an action to be transmitted is determined according to a monitoring result.

This enables a thoughtful transmission way such as presenting an action following a potential willingness in a natural way and giving the user a push.

Figure 14:
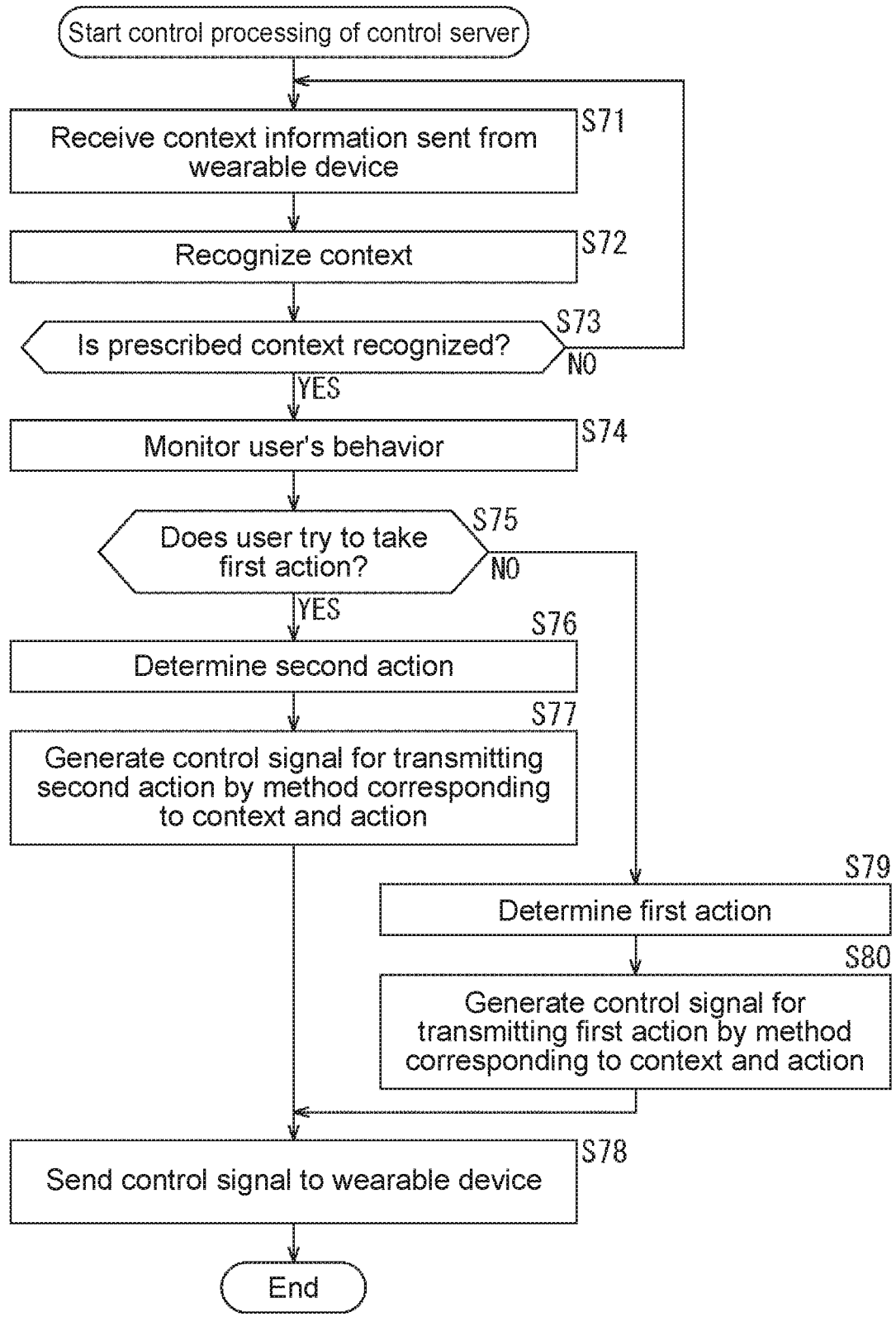
FIG. 14 is a flowchart for describing control processing of a control server according to a third embodiment.

Next, the control processing of the control server 2 will be described with reference to a flowchart of FIG. 14.

In Step S71, the context recognition unit 121 receives and acquires the context information sent from the wearable device 1.

In Step S72, the context recognition unit 121 recognizes the context on the basis of the acquired context information.

In Step S73, the context recognition unit 121 determines whether a prescribed context registered in the action database is recognized or not. When the context recognition unit 121 determines in Step S73 that a prescribed context is recognized, the processing proceeds to Step S74.

In Step S74, the context recognition unit 121 predicts a user's behavior by monitoring on the basis of the context information sequentially sent from the wearable device 1. In the wearable device 1, the context information is repetitively sent. Since an action is not yet transmitted, the user takes an action corresponding to the current context according to the user's will.

In Step S75, the action determination unit 122 determines whether the user tries to take the first action or not in the two actions corresponding to the context recognized by the context recognition unit 121, on the basis of a monitoring result.

In Step S75, when determining that the user tries to take the first action, the action determination unit 122 determines the second action as an action to be transmitted to the user in Step S76. Of the two actions managed in the action database as actions corresponding to the current context, one action different from the other action that the user tries to take is determined. Further, the action determination unit 122 refers to the action database to determine a transmission method for the second action.

In Step S77, the control signal generation unit 123 generates a control signal indicating the second action and the transmission method that are determined by the action determination unit 122.

In Step S78, the control signal generation unit 123 sends the control signal to the wearable device 1.

Meanwhile, in Step S75, when the action determination unit 122 determines that the user tries to take the second action instead of the first action, the processing proceeds to Step S79.

In Step S79, the action determination unit 122 determines the first action as an action to be transmitted to the user. In this case as well, of the two actions managed in the action database as actions corresponding to the current context, one action different from the other action that the user tries to take is determined. Further, the action determination unit 122 refers to the action database to determine a transmission method for the first action.

In Step S80, the control signal generation unit 123 generates a control signal indicating the first action and the transmission method that are determined by the action determination unit 122. The control signal generated here is sent to the wearable device 1 in Step S78.

In the wearable device 1, processing similar to the processing described with reference to FIG. 11 is performed, and an action opposite to the action that the user tries to take is transmitted as an action corresponding to the current context.

By the processing described above, when it is recognized that there is a piece of cake, if the user refrains from eating the piece of cake, an action of "eat" is determined and transmitted by using warm wind and sound of an angelic limpid tone. Conversely, if the user tries to eat the piece of cake, an action of "refrain from eating" is determined and transmitted by using cool wind and sound of a devil tone.

Further, when it is recognized that the user does not focus on the class, if the user tries to focus on the class, an action of "fall asleep" is determined and transmitted by using warm wind. Conversely, if the user tries to fall asleep, an action of "focus" is determined and transmitted by using cool wind.

When it is recognized that the other person looks tough, if the user tries to run away, an action of "stand against" is determined and transmitted by pushing the back with the robot arm unit 94. Conversely, if the user tries to stand against the other person, an action of "run away" is determined and transmitted by pulling the hair with the robot arm unit 94.

This also achieves a thoughtful transmission way in which two opposite actions are transmitted in a natural way.

Fourth Embodiment Method of Determining Action To Be Transmitted

It is assumed that an action is determined on the basis of the context information generated by the wearable device 1, but the method of determining an action to be transmitted to the user may be another method. An action determined by another method is also transmitted in a natural way by using various methods as described above.

FIG. 15 is a diagram showing an example of the action information.

The context of the context ID 4 is a context selected under the condition that it is recognized that a sender of e-mail is angry before the e-mail is opened (before the user reads the e-mail).

In this example, the feeling or situation of the sender is recognized from a message included in the e-mail to the user of the wearable device 1, and an action corresponding to a recognition result is determined. The feeling or situation of the sender corresponds to the feelings of other people around the user or the situations of other people around the user and is included in the above-mentioned context.

The e-mail to the user of the wearable device 1 is acquired by the control server 2 and the content thereof is analyzed. In the control server 2, information for recognition, such as key words (negative words/positive words) representing the feelings or situations of the sender, is managed. When receiving the e-mail to the user of the wearable device 1, the control server 2 performs natural language processing to extract key words and performs recognition of the feelings or situations of the sender on the basis of the frequencies of those words.

When it is recognized that the sender of the e-mail is angry, "reply immediately" is determined as an action to be transmitted to the user. Further, a method of generating vibration having a prescribed pattern and using sound of a quavering tone is determined as a transmission method for "reply immediately".

In such a manner, the context of the user can be determined also by a method different from the method using the context information generated by the wearable device 1.

It should be noted that the context may be recognized by using not only the message included in the e-mail but also a message of SNS (Social Networking Service) or the like as the message to the user of the wearable device 1.

Figure 16:
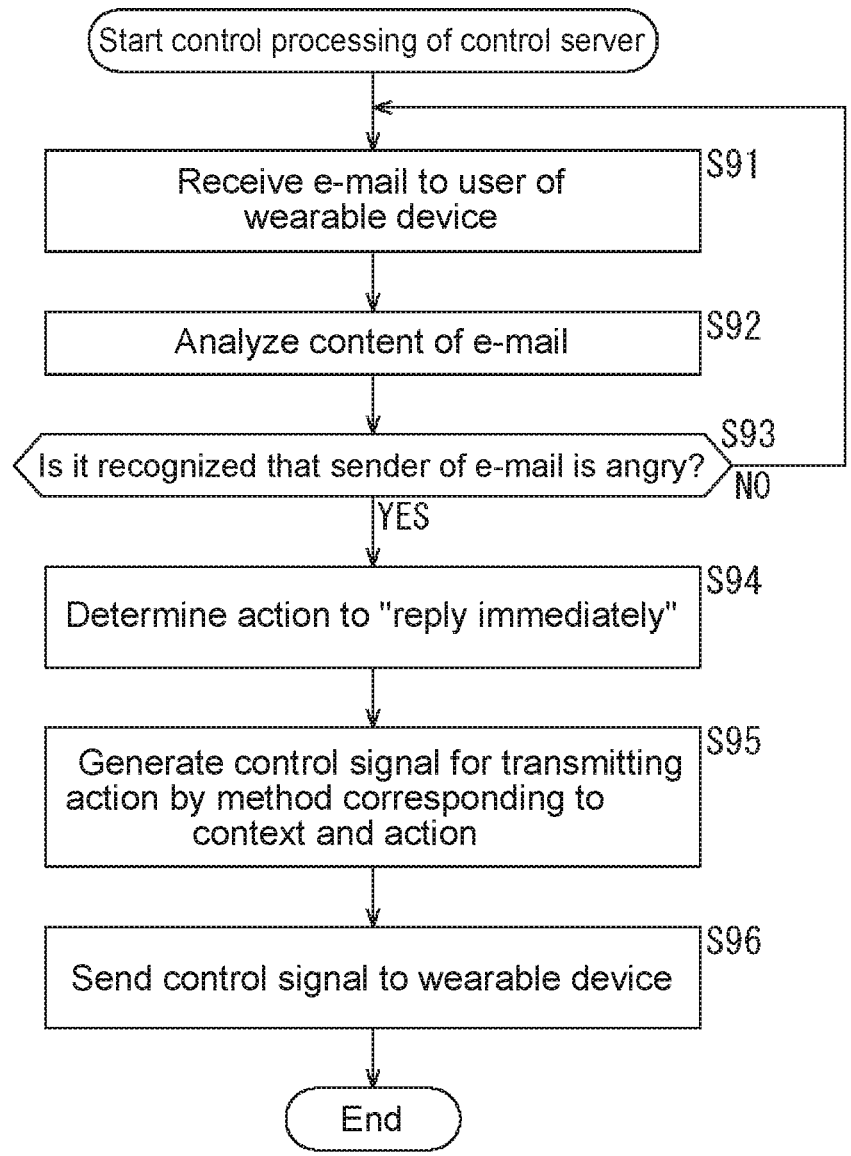
FIG. 16 is a flowchart for describing control processing of a control server according to a fourth embodiment.

Next, the control processing of the control server 2 will be described with reference to a flowchart of FIG. 16.

In Step S91, the context recognition unit 121 receives and acquires e-mail to the user of the wearable device 1. The e-mail to the user of the wearable device 1 may be acquired from an apparatus regularly used by the user for sending/receiving e-mail, or may be acquired from a mail server used by the user.

In Step S92, the context recognition unit 121 analyzes the content of the acquired e-mail and recognizes the context.

In Step S93, the context recognition unit 121 determines whether a prescribed context registered in the action database, e.g., the sender of the e-mail is angry, is recognized or not.

When the context recognition unit 121 determines that a prescribed context is not recognized in Step S93, the processing returns to Step S91 and the following processing is repeated. Meanwhile, when the context recognition unit 121 determines that a prescribed context is recognized in Step S93, the processing proceeds to Step S94.

In Step S94, the action determination unit 122 refers to the action database managed by the action information storage unit 113 and determines an action and a transmission method therefor that are suitable for the prescribed context. When the fact that "the sender of the e-mail is angry" is recognized, an action of "reply immediately" and a transmission method using vibration and sound of a quavering tone are determined.

In Step S95, the control signal generation unit 123 generates a control signal indicating the action and the transmission method that are determined by the action determination unit 122.

In Step S96, the control signal generation unit 123 sends the control signal to the wearable device 1.

In the wearable device 1 that has received the control signal, processing similar to the processing described with reference to FIG. 11 is performed, and "reply immediately" is transmitted to the user.

This allows the user of the wearable device 1 to recognize the need to "reply immediately" as an action suitable for the current context before confirming the content of the e-mail.

MODIFIED EXAMPLES

<1. Example of Action>

The actions described above as recognizable ones are examples. It is also possible to cause other actions to be recognized on the basis of the context information.

FIG. 17 is a diagram showing an example of the action information.

In the example of FIG. 17, a single action and a single transmission method are managed in association with the context of a context ID 5. Further, two actions and transmission methods for the respective actions are managed in association with the context of a context ID 6.

The context of the context ID 5 is a context selected under the condition that it is recognized that a customer looking at a product does not have a willingness to buy it. The context of the context ID 5 is recognizable, for example, when the user of the wearable device 1 is a salesperson for the product and is serving customers in a store.

It is recognized that a customer does not have a willingness to buy a product, when the front image included in the context information is analyzed. For example, assuming that a person who is seen by the user of the wearable device 1 is a customer, when a direction of the face, a motion of the line of sight, or a facial expression of the customer shows a peculiar pattern (feature) appearing when a customer does not have a willingness to buy a product, it is recognized that the customer does not have a willingness to buy the product. The fact that the customer looking at a product does not have a willingness to buy it is, for example, a recognition result of the surrounding environment of the user and the situations of other people around the user.

When it is recognized that the customer looking at a product does not have a willingness to buy it, "serve another customer" is determined as an action to be transmitted to the user as a salesperson. Further, a method using sound of a calm tone is determined as a transmission method for "serve another customer".

The context of the context ID 6 is a context selected under the condition that it is recognized that the user is tired from jogging.

It is recognized that the user is jogging, for example, when vibration indicated by the sensor data included in the context information shows a peculiar pattern appearing during jogging. Further, it is recognized that the user is tired, for example, when the heart rate of the user indicated by the sensor data included in the context information shows a peculiar pattern appearing when the user is tired. The fact that the user is tired from jogging is, for example, a recognition result of the situation of the user.

When it is recognized that the user is tired from jogging, two opposite actions of "try a little harder" and "rest" are determined as actions to be transmitted to the user.

Further, a method of tapping the back of the user with the robot arm unit 94 and using a male voice of a forceful tone is determined as a transmission method for "try a little harder". Meanwhile, a method of gently stroke the back of the user with the robot arm unit 94 and using a female voice of a gentle tone is determined as a transmission method for "rest".

In such a manner, it is possible to recognize various actions in the control server 2.

When the relationship between the context and the action is not fixed and a certain context is recognized, a single action may be determined from various actions at random and transmitted.

In this case, the user may be allowed to evaluate the action determined at random. The evaluation of the action is performed by, for example, operating the operation unit 33 located near the ear lobe when the user wears the wearable device 1. The evaluation of the action input by the user is used for determining an action when the same context is recognized as the next context, such as a change in priority order.

The transmission method for each action can also be changed. For example, the action transmitted by the method using wind may be transmitted by a method using vibration, a method using sound, or a method using the robot arm unit 94. In such a manner, the method used for transmitting an action can be changed and a combination thereof can also be changed.

Further, it is possible to transmit an action by using various methods capable of stimulating the five senses, such as a method using smell, a method using water, and a method using heat. Transmission of an action may be performed by projecting videos or texts by the projection unit 25.

<2. Another Configuration Example of Information Processing System>

Figure 18:
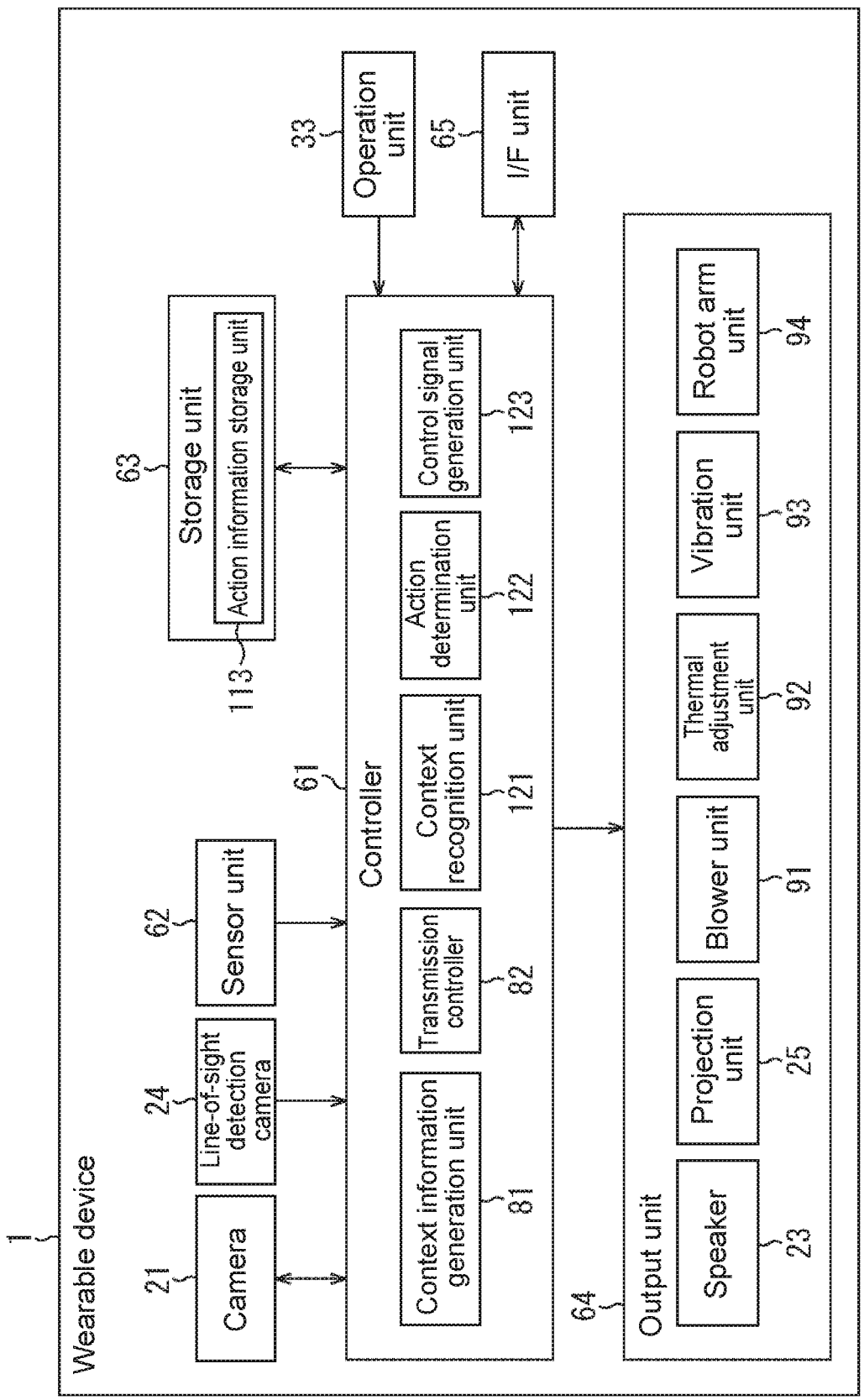
FIG. 18 is a diagram showing a configuration example of the wearable device.

FIG. 18 is a diagram showing a configuration example of the wearable device 1 as an information processing system. The same configuration as that described with reference to FIGS. 6 and 7 is denoted by the same reference symbol. Overlapping description will be appropriately omitted.

In the example of FIG. 18, the functions, which have been described as those of the control server 2, are implemented in the wearable device 1. In other words, the CPU executes a predetermined program, and thus in addition to the context information generation unit 81 and the transmission controller 82, the context recognition unit 121, the action determination unit 122, and the control signal generation unit 123 are achieved in the controller 61.

The context recognition unit 121 of the controller 61 acquires the context information generated by the context information generation unit 81 and recognizes the context of the user.

The action determination unit 122 refers to the action database managed by the action information storage unit 113 formed in the storage unit 63 to determine an action corresponding to the context recognized by the context recognition unit 121 and a transmission method therefor.

The control signal generation unit 123 generates a control signal indicating the action and the transmission method that are determined by the action determination unit 122. The control signal generated by the control signal generation unit 123 is supplied to the transmission controller 82 and used for driving each unit.

In the wearable device 1 having the configuration of FIG. 18, each type of processing including the recognition of a context, the determination of an action corresponding to the context, and the determination of a transmission method, which have been described as those performed by the control server 2, is performed. In such a manner, at least part of the functions of the control server 2 can be achieved in the wearable device 1.

<3. Example of Outer Appearance of Wearable Device>

Ear-Hook Type

Figure 19A:
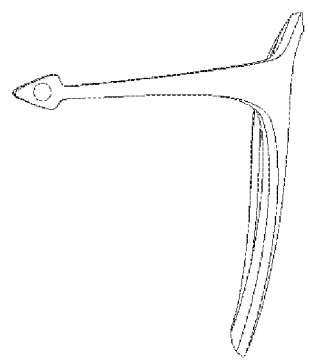
FIGS. 19A and 19B are views showing an outer appearance of an ear-hook wearable device.
Figure 19B:
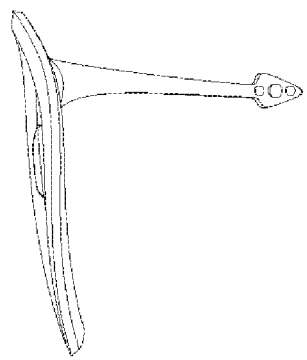

FIGS. 19A and 19B are views showing an outer appearance of the wearable device 1. In FIGS. 19A and 19B, reference symbols representing the respective units are omitted. The same holds true for FIGS. 20A, 20B, 21A, 21B, 22, 23A, and 23B. FIG. 19A shows the front of the wearable device 1, and FIG. 19B shows the rear of the wearable device 1.

Figure 20A:
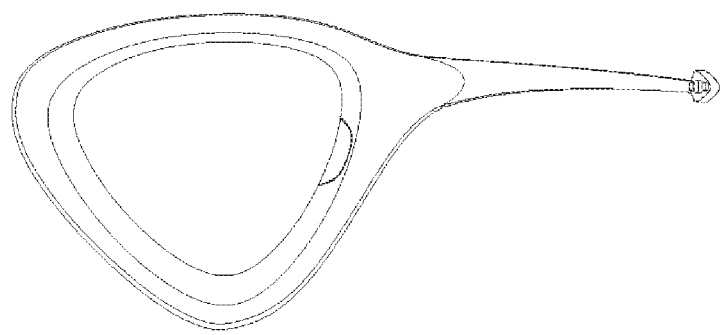
FIGS. 20A and 20B views showing the outer appearance of the ear-hook wearable device.
Figure 20B:
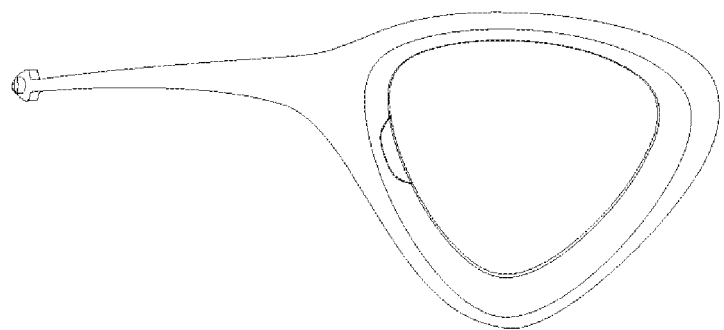

FIGS. 20A and 20B are another views showing the outer appearance of the wearable device 1. FIG. 20A shows a left side surface of the wearable device 1, and FIG. 20B shows a right side surface of the wearable device 1.

Figure 21A:
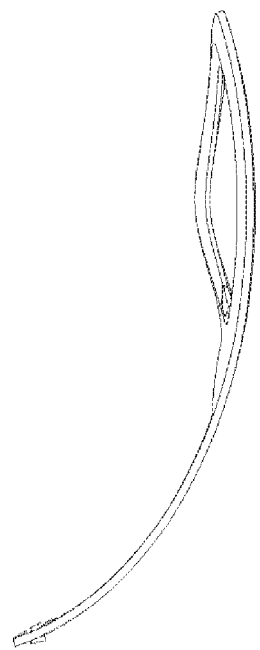
FIGS. 21A and 21B are views showing the outer appearance of the ear-hook wearable device.
Figure 21B:
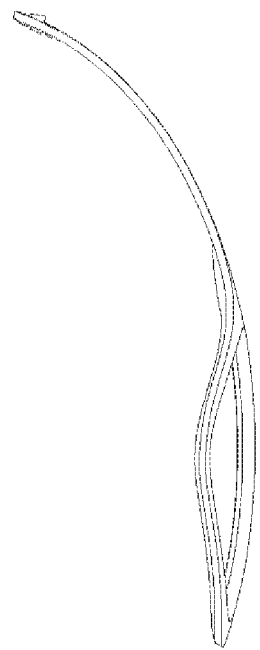

FIGS. 21A and 21B are still another views showing the outer appearance of the wearable device 1. FIG. 21A shows a top surface of the wearable device 1, and FIG. 21B shows a bottom surface of the wearable device 1.

Figure 22:
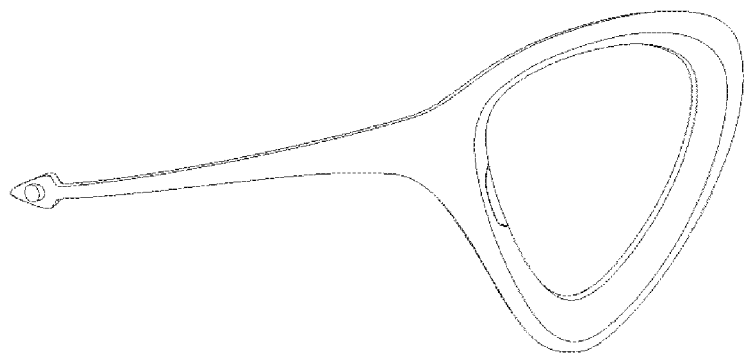
FIG. 22 is a view showing the outer appearance of the ear-hook wearable device.
Figure 23A:
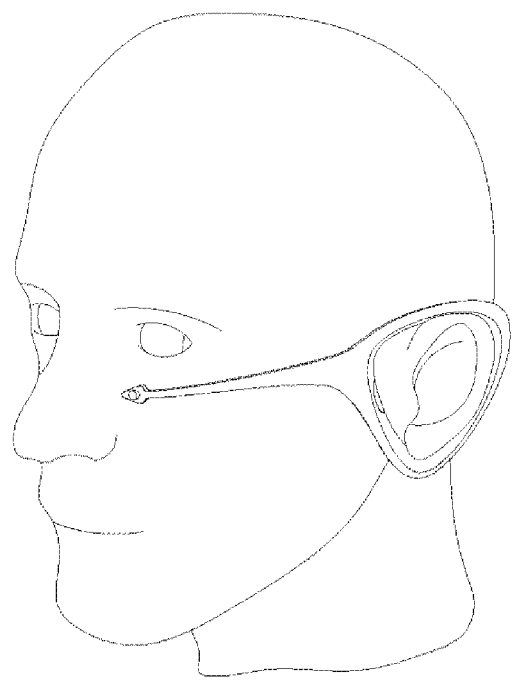
FIGS. 23A and 23B are views showing a mount example of the ear-hook wearable device.
Figure 23B:
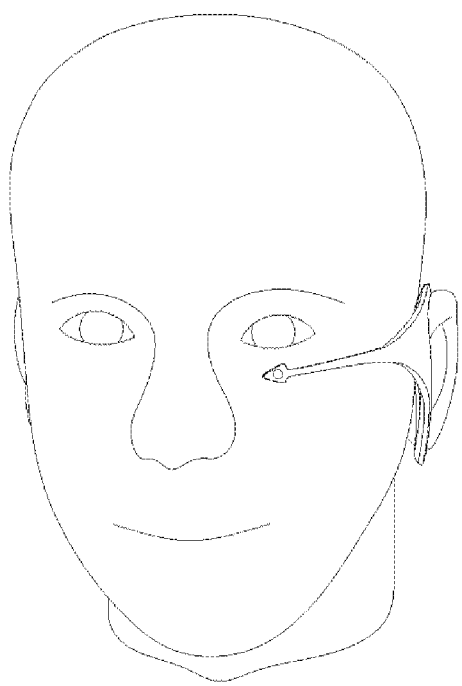

FIG. 22 is a perspective view showing the outer appearance of the wearable device 1. FIGS. 23A and 23B are views showing a mounted state of the wearable device 1. The wearable device 1 is mounted such that the left ear passes through the opening 11a of the ear hook portion 11A.

The wearable device 1 has a function of presenting information by a retina-direct-projection system, a function of reproducing sound including voice, a function of imaging the front by the front imaging camera 21, a function of detecting the line of sight based on an image captured by the line-of-sight detection camera 24, and the like in addition to the behavior support function described above.

Shoulder-Mounted Type

Hereinabove, the wearable device that performs the behavior support for the user is assumed as an ear-hook device, but the form of the wearable device is optional.

Figure 24:
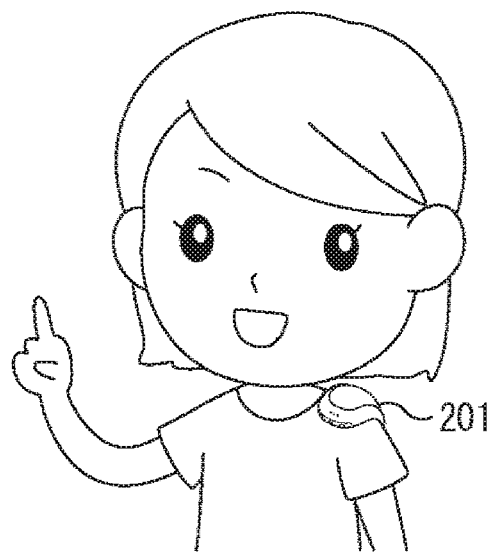
FIG. 24 is a view showing a mount example of a shoulder-mounted wearable device.

FIG. 24 is a view showing a mount example of another wearable device.

A wearable device 201 shown in FIG. 24 is a shoulder-mounted agent device. The wearable device 201 performs the behavior support for the user as a wearer, in a similar manner as in the wearable device 1.

Figure 25:
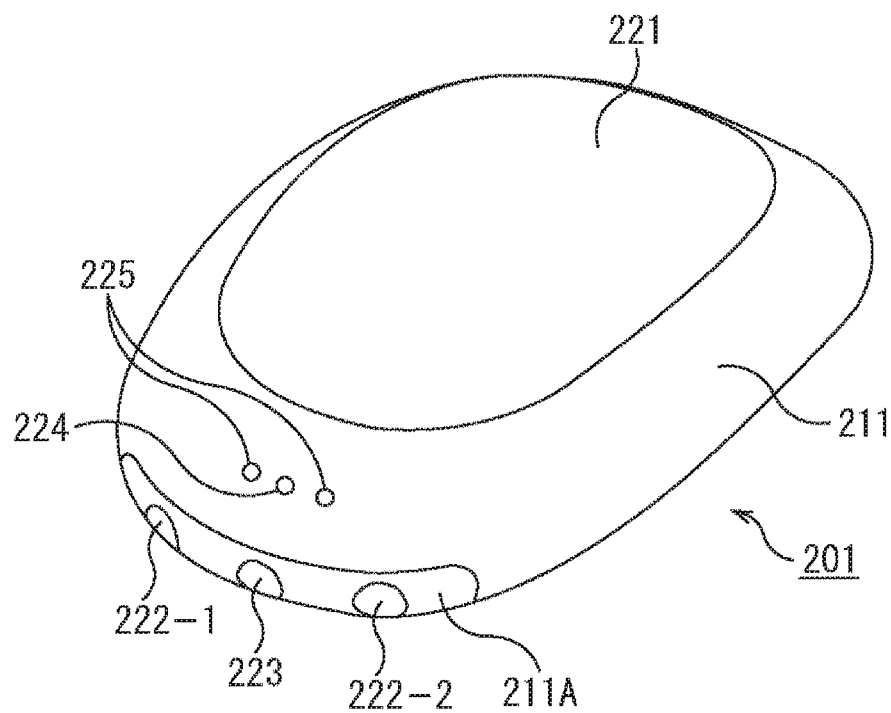
FIG. 25 is a view showing an outer appearance of the shoulder-mounted wearable device.

FIG. 25 is a view showing an example of an outer appearance of the wearable device 201.

Figure 26:
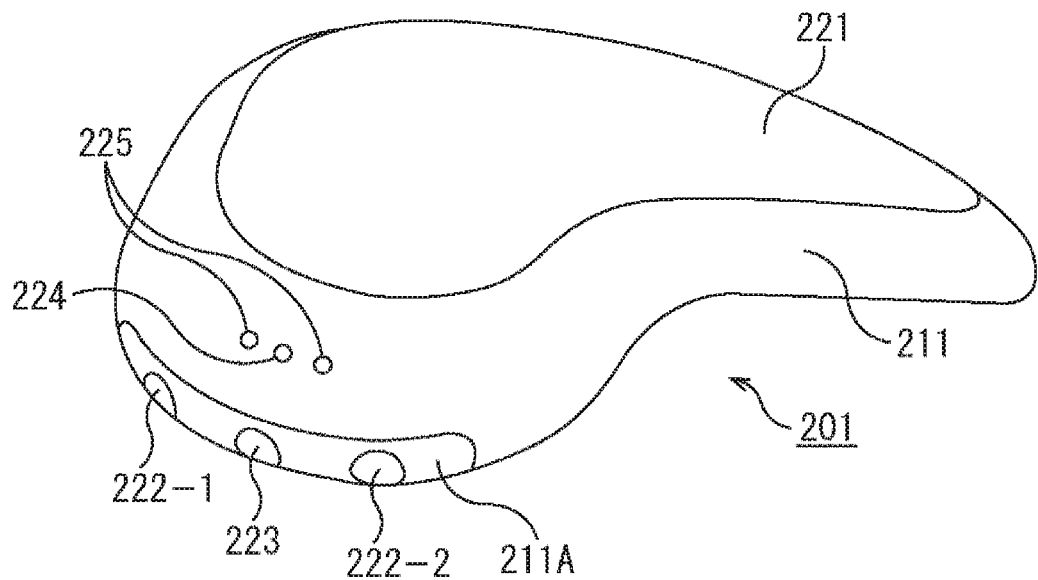
FIG. 26 is a view showing the outer appearance of the shoulder-mounted wearable device.

The wearable device 201 has a substantially elliptical shape in plan view and includes a casing 211 having a flat dome shape. At least part of the casing 211 is made of an elastic material. The casing 211 has flexibility, bends by the user applying force from the upper surface or by its dead weight, and deforms as shown in FIG. 26 to become stable on the shoulder of the user. Japanese Patent Application Laid-open No. 2013-89219 discloses a device in which a deformable material is used, and the mechanism similar thereto can be employed for the casing 211.

The upper surface of the casing 211 has a gentle arc-shape. At the center of the upper surface of the casing 211, a display 221 having a substantially elliptical shape in plan view is formed.

Three small circles are disposed side by side at a circumferential portion of the display 221 on the front side. The center small circle configures a microphone 224, and the left and right small circles configure speakers 225.

A section 221A having a horizontally elliptical shape when viewed from the front is formed on the front surface of the casing 211. Cameras 222-1 and 222-2 that configure stereo cameras, and a projector 223 are provided on the inner side of the section 221A.

Figure 27:
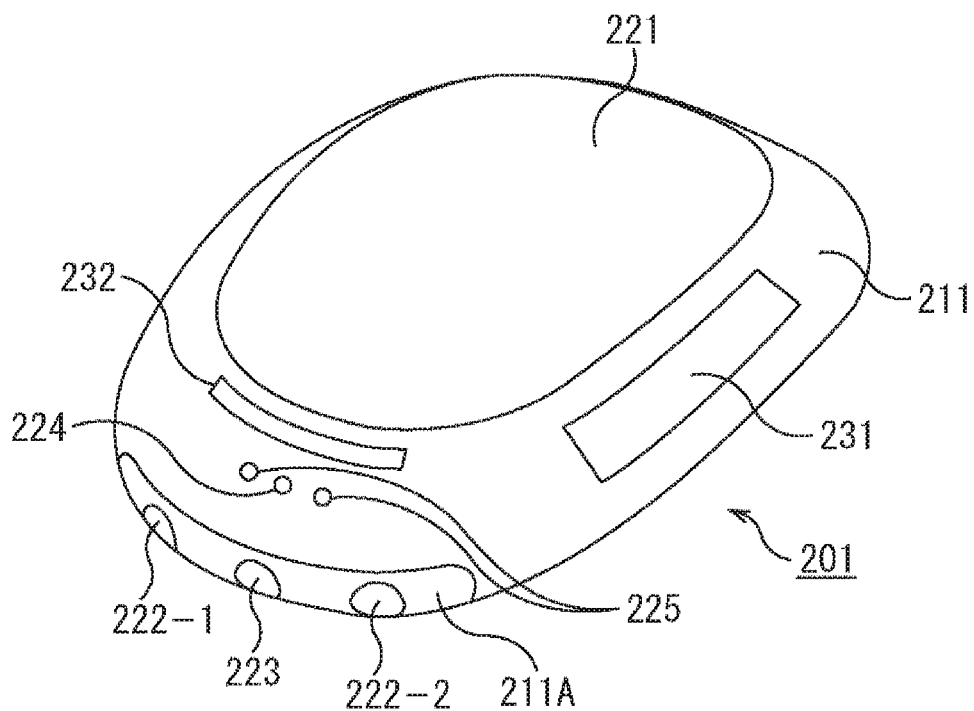
FIG. 27 is a view showing the outer appearance of the shoulder-mounted wearable device.

FIG. 27 is a view showing another example of the outer appearance of the wearable device 201.

In the example of FIG. 27, an attachment portion 231 is provided at a circumferential portion on the right-side-surface side of the display 221. A small robot arm to be used for transmitting an action is attachable to the attachment portion 231. Further, an outlet 232 to be an outlet of wind used for transmitting an action is provided at a circumferential portion of the display 221 on the front side.

As with the case of the wearable device 1, the wearable device 201 of FIG. 27 transmits an action by appropriately combining a method using wind, a method using vibration, a method using sound, and a method using the robot arm. The wearable device 201 also has the same configuration as that described with reference to FIG. 6 or 18.

In such a manner, transmitting an action in a natural way by using wind or the like can be performed by the shoulder-mounted wearable device 201. With the shoulder-mounted wearable device 201, various actions can be transmitted from a position near the ear or neck.

The wearable device 201 may be allowed to move in the vicinity of the shoulder. In this case, the user wears a pad made of a magnetic material on the shoulder. The wearable device 201 generates a magnetic force and moves within the range of the pad, thus transmitting various actions. The wearable device 201 may have a function of flying.

Figure 28A:
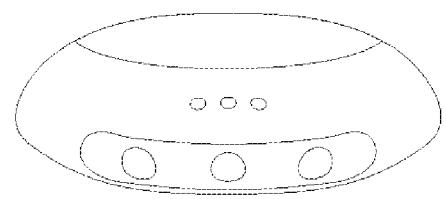
FIGS. 28A and 28B are views showing the outer appearance of the shoulder-mounted wearable device.
Figure 28B:
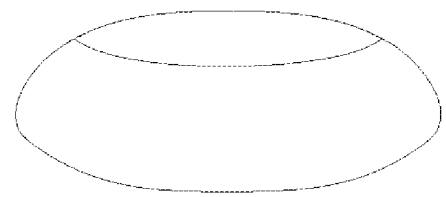

FIGS. 28A and 28B are views showing an outer appearance of the wearable device 201. In FIGS. 28A and 28B, reference symbols representing the respective units are omitted. The same holds true for FIGS. 29A, 29B, 30A, 30B, and 31. FIG. 28A shows the front of the wearable device 201, and FIG. 28B shows the rear of the wearable device 1.

Figure 29A:
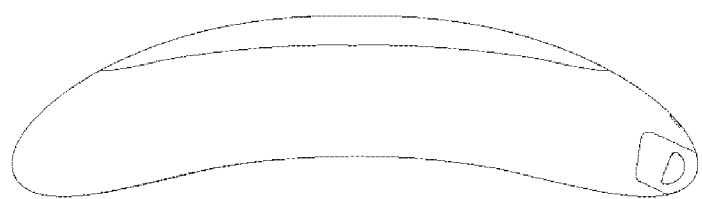
FIGS. 29A and 29B are views showing the outer appearance of the shoulder-mounted wearable device.
Figure 29B:
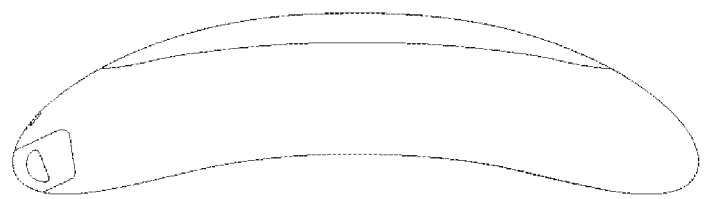

FIGS. 29A and 29B are another views showing the outer appearance of the wearable device 201 FIG. 29A shows a left side surface of the wearable device 201, and FIG. 29B shows a right side surface of the wearable device 201. The casing 211 is formed into a gentle arc-shape when viewed from the side surface.

Figure 30A:
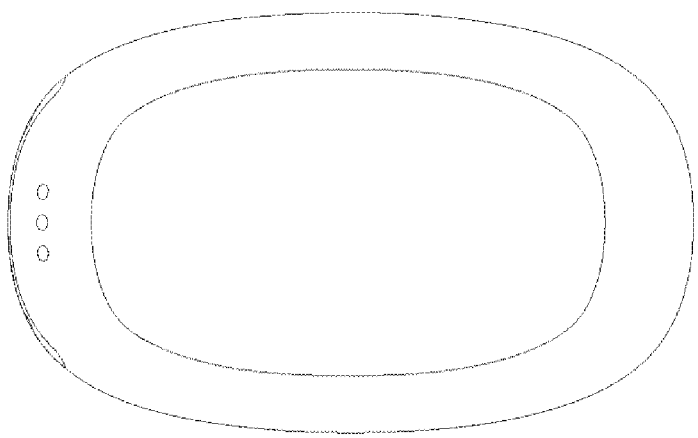
FIGS. 30A and 30B are views showing the outer appearance of the shoulder-mounted wearable device.
Figure 30B:
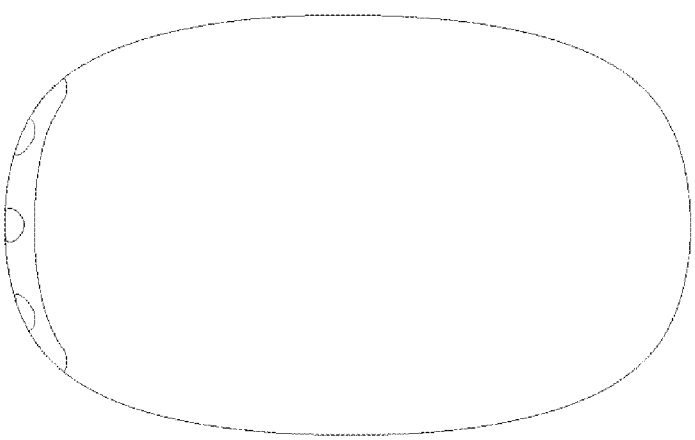

FIGS. 30A and 30B are still another views showing the outer appearance of the wearable device 201. FIG. 30A shows a top surface of the wearable device 201, and FIG. 30B shows a bottom surface of the wearable device 201.

Figure 31:
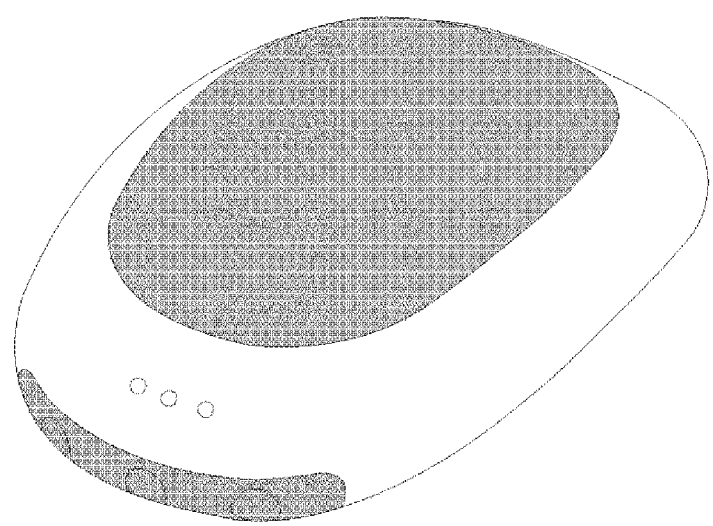
FIG. 31 is a view showing the outer appearance of the shoulder-mounted wearable device.

FIG. 31 is a perspective view showing the outer appearance of the wearable device 201. In FIG. 31, a gray-colored portion represents a transparent portion. A transparent cover is fitted into each of the section 211A and the display 221.

The wearable device 201 has a function of presenting information by the display 221 or the projector 223, a function of reproducing sound including voice, a function of imaging the front by the cameras 222-1 and 222-2, and the like in addition to the behavior support function described above.

Neck-Hanging Type

Figure 32:
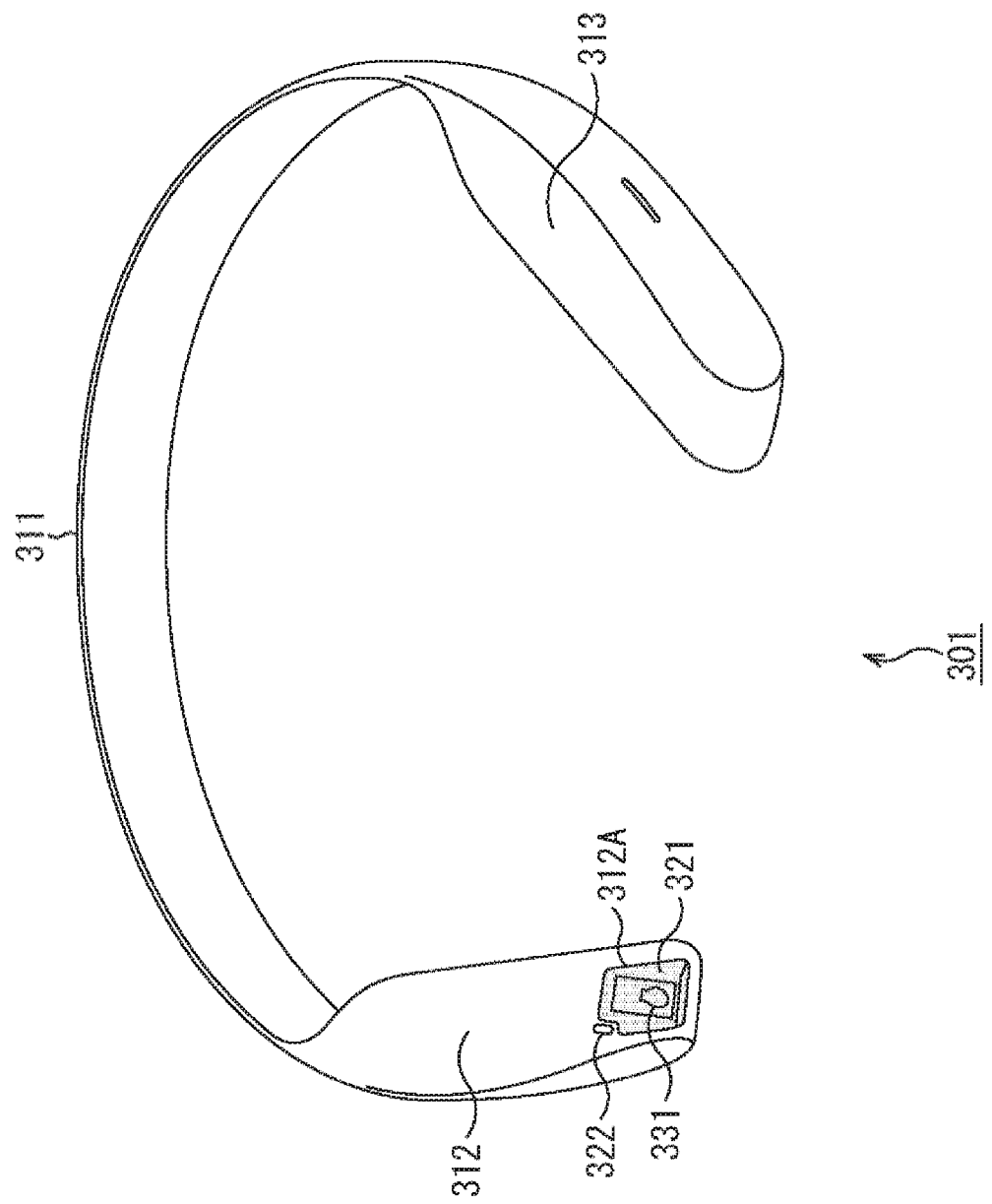
FIG. 32 is a view showing an outer appearance of a neck-hanging wearable device.

FIG. 32 is a view showing a configuration example of an outer appearance of a wearable device 301 as a neck-hanging wearable device.

The wearable device 301 is also an agent device that performs the behavior support for the user as a wearer, in a similar manner as in the wearable device 1.

As shown in FIG. 32, the wearable device 301 has a substantially C-shaped outer appearance as a whole when viewed from the front. The wearable device 301 is configured by providing a right-side unit 312 and a left-side unit 313 on the inner side of a band portion 311 at positions close to the right tip and the left tip thereof, respectively, the band portion 311 being a curved, thin plate-like member.

The right-side unit 312 shown on the left side of FIG. 32 includes a casing having a width larger than the thickness of the band portion 311 when viewed from the front, and is formed so as to swell from the inner surface of the band portion 311.

Meanwhile, the left-side unit 313 shown on the right side has a shape that is substantially symmetrical to the right-side unit 312 such that the opening on the front of the band portion 311 is sandwiched therebetween. The left-side unit 313 includes a casing having a width larger than the thickness of the band portion 311 when viewed from the front, and is formed so as to swell from the inner surface of the band portion 311, as in the right-side unit 312.

The wearable device 301 having such an outer appearance is worn around the neck. When the wearable device 301 is worn, the inner side of the innermost portion of the band portion 311 abuts on the back of the neck of the user, and the wearable device 301 takes a tilted posture. When viewed from the user, the right-side unit 312 is positioned on the right side of the bottom of the neck of the user, and the left-side unit 313 is positioned on the left side of the bottom of the neck of the user.

The wearable device 301 has an imaging function, a music reproduction function, a wireless communication function, a sensing function, and the like, in addition to the behavior support function described above.

The user operates a button provided to the right-side unit 312 by, for example, the right hand and operates a button provided to the left-side unit 313 by, for example, the left hand while wearing the wearable device 301, and can thus execute functions thereof. Further, the wearable device 301 also implements a sound recognition function. The user can also operate the wearable device 301 by utterance.

By the music reproduction function of the wearable device 301, music output from the speaker provided to the right-side unit 312 mainly reaches the right ear of the user, and music output from the speaker provided to the left-side unit 313 mainly reaches the left ear of the user.

The user can run or ride a bicycle while wearing the wearable device 301 and listening to music. Instead of music, sound of various pieces of information such as news acquired via a network may be output.

In such a manner, the wearable device 301 is a device assumed to be utilized during light exercise. Since the ears are not closed by wearing of earphones or the like, the user can listen to music output from the speakers and also hear ambient sound.

Each of the right-side unit 312 and the left-side unit 313 has a curved surface having an arc-shape formed at the tip thereof. A substantially vertically long rectangular aperture 312A is formed at the tip of the right-side unit 312 from a position close to the front side of the upper surface to a position close to the upper side of the curved surface of the tip. The aperture 312A has a shape whose upper left corner is recessed, and an LED (Light Emitting Diode) 322 is provided at that recessed position.

A transparent cover 321 made of acrylic or the like is fit into the aperture 312A. The surface of the cover 321 forms a curved surface having substantially the same curvature as that of the curved surface of the left-side unit 313 at the tip. In the depth of the cover 321, a lens 331 of a camera module provided to the inside of the right-side unit 312 is disposed. An imaging direction of the camera module is a front direction of the user when viewed from the user wearing the wearable device 301.

The user can photograph a forward landscape as a moving image or a still image when wearing the wearable device 301 and also running or riding a bicycle while listening to music as described above. Further, the user can perform such photographing by a sound command in a handsfree manner.

Figure 33:
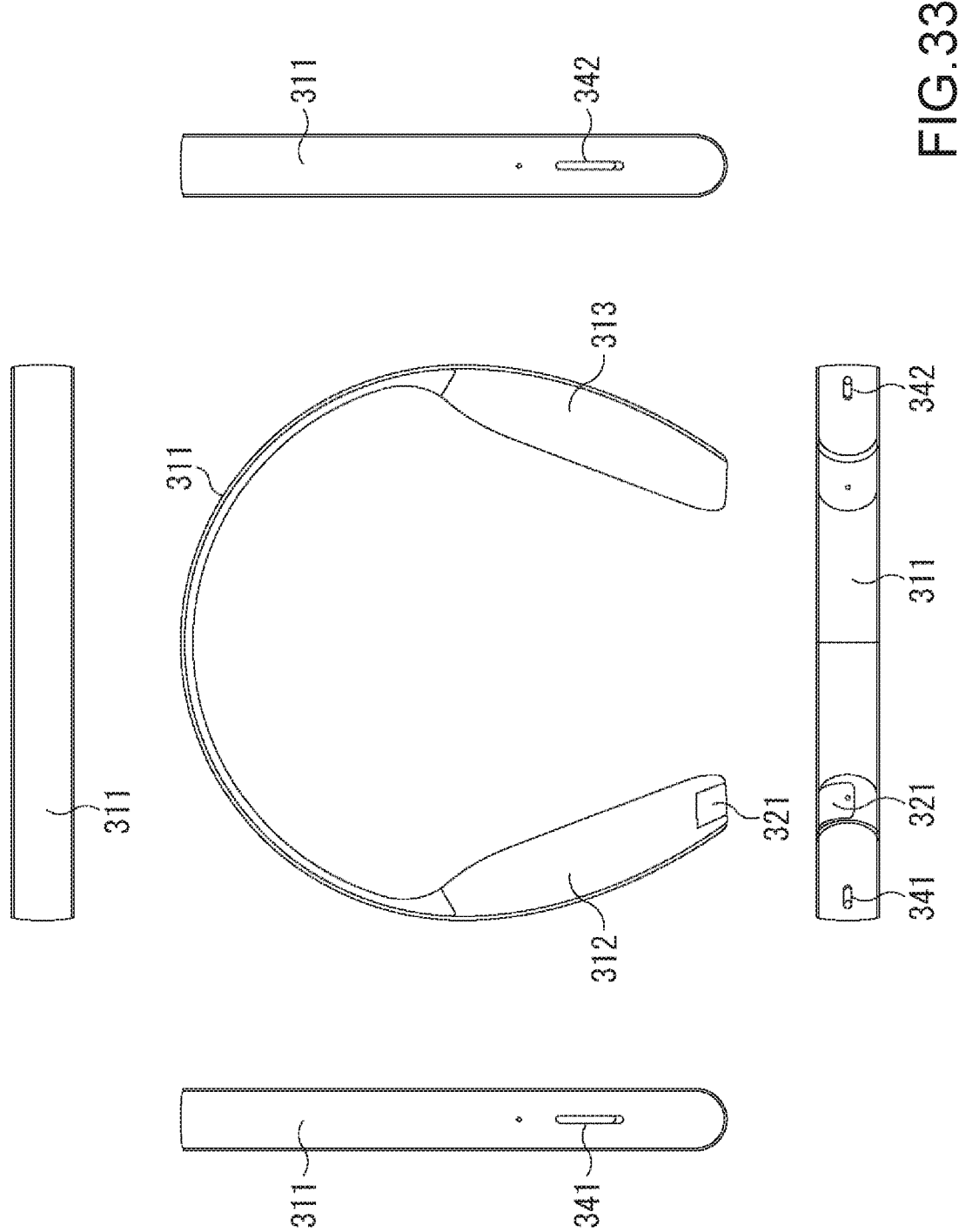
FIG. 33 is a view showing the outer appearance of the neck-hanging wearable device.
Figure 34:
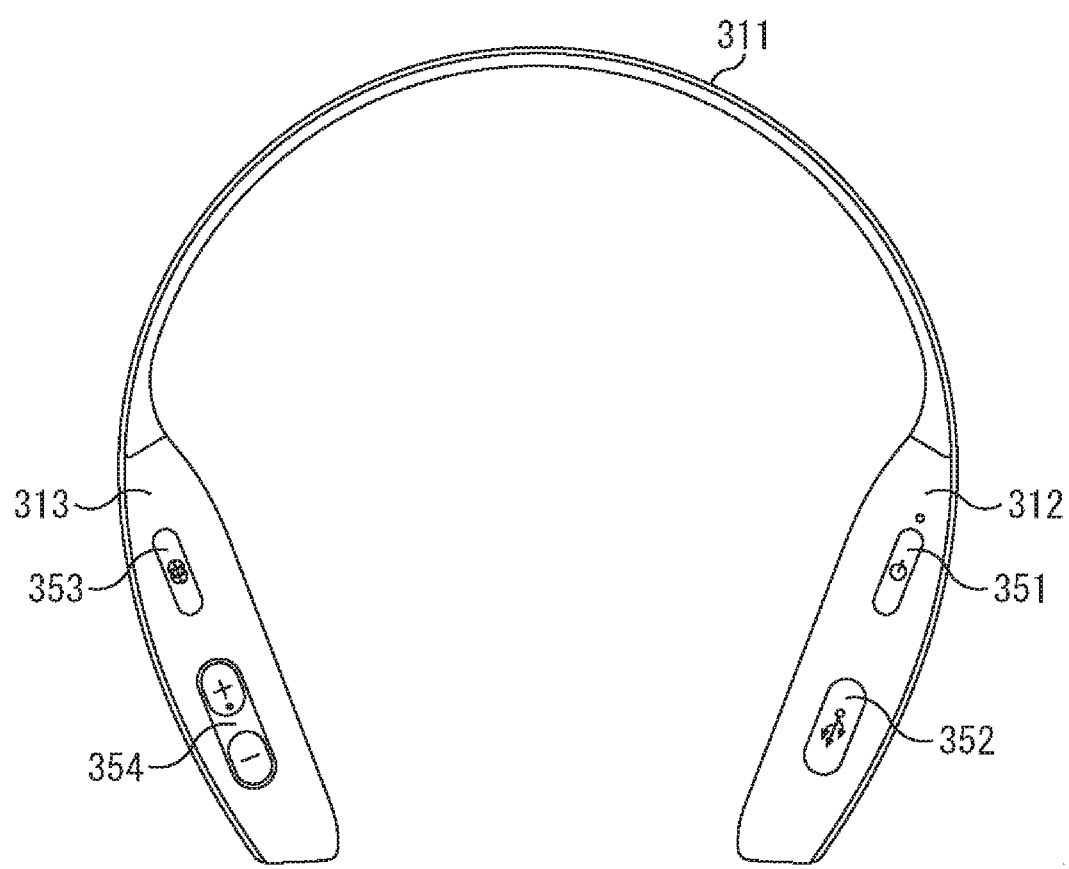
FIG. 34 is a view showing the outer appearance of the neck-hanging wearable device.

FIGS. 33 and 34 are views each showing the outer appearance of the wearable device 301.

FIG. 33 shows the outer appearance of the wearable device 301 at the center when viewed from the front. As shown in FIG. 33, a speaker hole 341 is formed on the left side surface of the wearable device 301, and a speaker hole 342 is formed on the right side surface thereof.

As shown in FIG. 34, a power supply button 351 and a USB terminal 352 are provided on the rear surface of the right-side unit 312. For example, a cover made of resin is put over the USB terminal 352.

A custom button 353 to be operated when various settings are performed, and a sound volume button 354 to be operated when a sound volume is adjusted are provided on the rear surface of the left-side unit 313.

Figure 35:
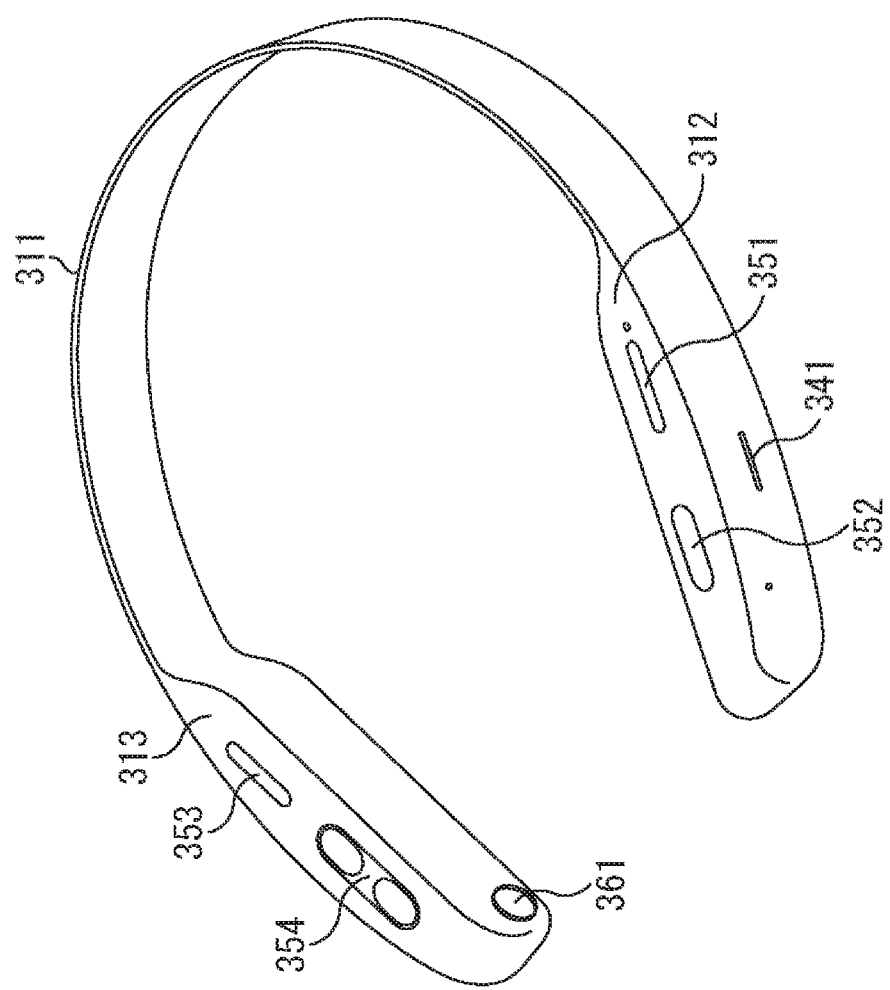
FIG. 35 is a view showing the outer appearance of the neck-hanging wearable device.

Further, as shown in FIG. 35, an assist button 361 is provided in the vicinity of the tip of the left-side unit 313 on the inner side thereof. A predetermined function such as the end of capturing of a moving image is assigned to the assist button 361.

In such a manner, the mode of the wearable device that performs behavior support can be changed. The above-mentioned behavior support may be performed by a wristwatch type wearable device or a ring-type wearable device. Further, the above-mentioned technology is also applicable not to a device carried while being mounted to a body but to a device such as a mobile phone carried by the hand.

<4. Configuration Example of Computer>

The series of processing described above can be executed by hardware or executed by software. In a case where the series of processing is executed by software, programs constituting the software are installed from a program recording medium in a computer incorporated in dedicated hardware, a general-purpose personal computer, or the like.

Figure 36:
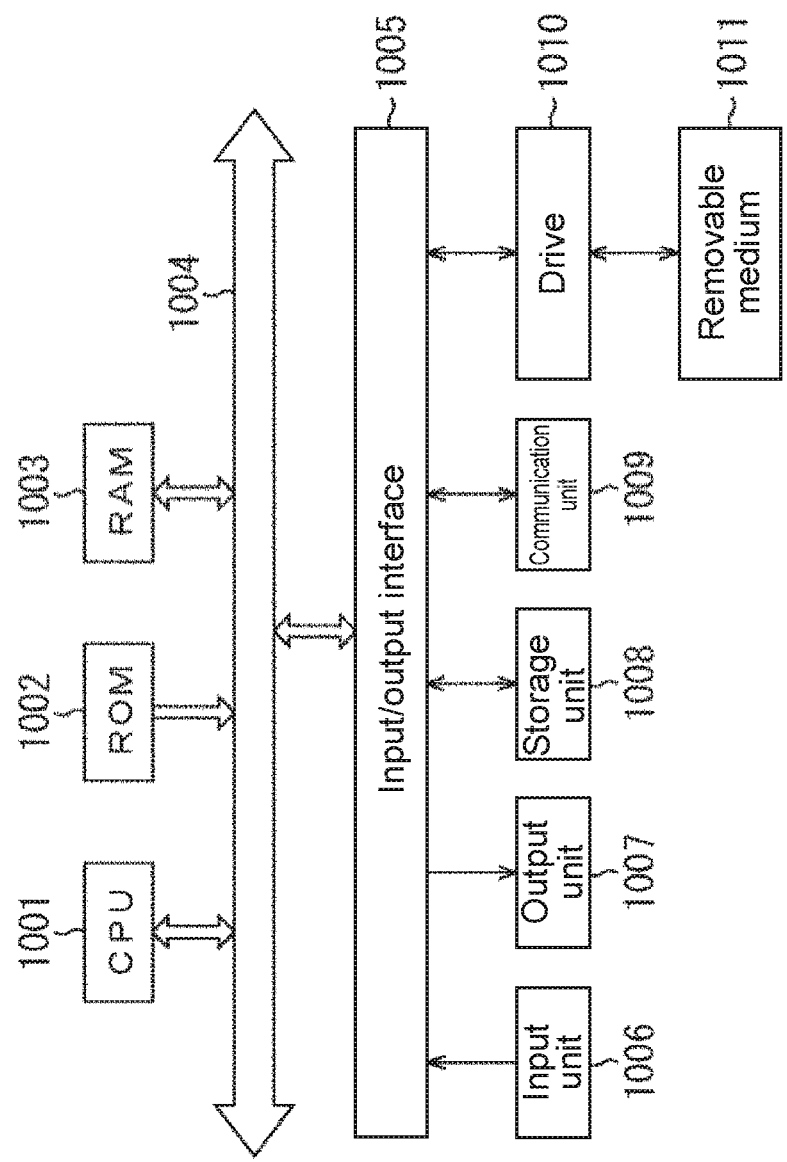
FIG. 36 is a block diagram showing a configuration example of a computer.

FIG. 36 is a block diagram showing a hardware configuration example of a computer that executes a program by the above-mentioned series of processing.

A CPU (Central Processing Unit) 1001, a ROM (Read Only Memory) 1002, and a RAM (Random Access Memory) 1003 are connected to one another by a bus 1004.

An input/output interface 1005 is further connected to the bus 1004. An input unit 1006 including a keyboard, a mouse, and the like, and an output unit 1007 including a display, a speaker, and the like are connected to the input/output interface 1005. Further, a storage unit 1008 including a hard disk, a nonvolatile memory, and the like, a communication unit 1009 including a network interface and the like, and a drive 1010 that drives a removable medium 1011 are connected to the input/output interface 1005.

In the computer configured as described above, the CPU 1001 loads the program stored in, for example, the storage unit 1008 to the RAM 1003 via the input/output interface 1005 and the bus 1004 and executes the program, to thus perform the series of processing described above.

The program to be executed by the CPU 1001 is provided by, for example, being recorded on the removable medium 1011, or provided via a wired or wireless transmission medium such as a local area network, the Internet, and digital broadcasting, to thus be installed in the storage unit 1008.

It should be noted that the program executed by the computer may be a program that is processed chronologically along the described order in this specification or may be a program that is processed in parallel or at a necessary timing such as when an invocation is performed.

In this specification, a system means an aggregation of a plurality of constituent elements (apparatus, module (parts), and the like), regardless of whether all constituent elements are included in the same casing or not. Therefore, a plurality of apparatuses accommodated in separate casings and connected to one another via a network is a system, and one apparatus including a plurality of modules in one casing is also a system.

The effects disclosed herein are merely exemplary ones and are not restrictive ones, and any other effects may be produced.

The embodiments of the present technology are not limited to the above-mentioned embodiments and can be variously modified without departing from the gist of the present technology.

For example, the present technology can have a configuration of cloud computing in which a plurality of apparatuses share one function and cooperate to perform processing via a network.

Further, the steps described in the flowchart described above can be executed by one apparatus or shared and executed by a plurality of apparatuses.

In addition, in a case where one step includes a plurality of processing steps, the plurality of processing steps in the one step can be executed by one apparatus or shared and executed by a plurality of apparatuses.

<5. Combination Example of Configurations>

The present technology can have the following configurations.

(1) An information processing system, including:
an acquisition unit that acquires context information representing at least one of a surrounding environment of a user having a device, a feeling of the user, a situation of the user, feelings of other people around the user, or situations of the other people; and
a controller that
recognizes a context of the user on a basis of the context information,
determines an action corresponding to the context, and
determines a transmission method for the action to the user, the transmission method being suitable for the context and the action.

(2) The information processing system according to (1), in which
the controller transmits the action corresponding to the context to the user by the determined transmission method.

(3) The information processing system according to (2), further including
a storage unit that stores a database in which a plurality of actions including a first action and a second action are registered in association with the single context.

(4) The information processing system according to (3), in which
when the controller recognizes the context of the user on a basis of the context information, the controller
determines one of the first action and the second action as the action corresponding to the context,
determines the transmission method suitable for the context and the one of the first action and the second action, and
transmits the one of the first action and the second action to the user by the determined transmission method.

(5) The information processing system according to (3), in which
the first action and the second action are registered in the database in association with the single context, the first action and the second action having opposite types of content, and
when the controller recognizes the context of the user on a basis of the context information, the controller
determines the first action and the second action having the opposite types of content as the actions corresponding to the context,
determines the transmission methods for the first action and the second action, and
transmits the first action and the second action to the user by the respective determined transmission methods.

(6) The information processing system according to (3), in which
the controller
predicts a behavior of the user on a basis of the context information that is acquired after the context of the user is recognized on a basis of the context information,
selects one of the first action and the second action that are associated with the context, depending on a predicted result of the behavior of the user, and
determines the transmission method suitable for the context and the selected action.

(7) The information processing system according to any one of (1) to (6), further including
a communication unit that receives the context information sent from the device, in which
the controller controls the communication unit to send a control signal to the device, the control signal indicating that the action corresponding to the context is to be transmitted to the user by the transmission method.

(8) The information processing system according to (1), in which
the controller analyzes content of a message to the user and recognizes the context of the user depending on an analyzed result.

(9) The information processing system according to any one of (1) to (8), in which
the transmission method is a method including at least one of a method using wind, a method using vibration, a method using sound, or a method using drive of a robot arm provided to the device.

(10) The information processing system according to (9), in which
the method using wind is a transmission method of sending wind having a temperature corresponding to the action to be transmitted.

(11) The information processing system according to (9), in which
the method using vibration is a transmission method of vibrating in a pattern corresponding to the action to be transmitted.

(12) The information processing system according to (9), in which
the method using sound is a transmission method of using sound of a tone corresponding to the action to be transmitted.

(13) The information processing system according to (9), in which
the method using the drive of the robot arm is a transmission method of pulling hair or pushing back of the user wearing the device.

(14) The information processing system according to any one of (1) to (13), in which
the device is wearable by being hooked on an ear, and
at least a part of an ear hook portion formed in the device is made of a material that deforms depending on a body temperature of the user.

(15) The information processing system according to any one of (1) to (13), in which
the device is wearable by being put on a shoulder of the user, and
at least a part of a casing of the device is made of a material that is flexible and deformable.

(16) A recording medium recording a program causing a computer to execute processing including the steps of:
acquiring context information representing at least one of a surrounding environment of a user having a device, a feeling of the user, a situation of the user, feelings of other people around the user, or situations of the other people;
recognizing a context of the user on a basis of the context information;
determining an action corresponding to the context; and
determining a transmission method for the action to the user, the transmission method being suitable for the context and the action.

(17) An information processing method, including the steps of:
acquiring context information representing at least one of a surrounding environment of a user having a device, a feeling of the user, a situation of the user, feelings of other people around the user, or situations of the other people;
recognizing a context of the user on a basis of the context information;
determining an action corresponding to the context; and
determining a transmission method for the action to the user, the transmission method being suitable for the context and the action.

(18) An information processing system, including:
a control server including
a communication unit that receives context information representing at least one of a surrounding environment of a user having a device, a feeling of the user, a situation of the user, feelings of other people around the user, or situations of the other people, the context information being sent from the device, and
a controller that
recognizes a context of the user on a basis of the context information,
determines an action corresponding to the context,
determines a transmission method for the action to the user, the transmission method being suitable for the context and the action, and
controls the communication unit to send a control signal to the device, the control signal indicating that the action corresponding to the context is to be transmitted to the user by the transmission method; and
the device including
a generation unit that generates the context information and sends the context information to the control server,
a communication unit that receives the control signal sent from the control server,
an output unit that transmits the action to the user, and
a controller that controls, according to the control signal, the output unit to transmit the action to the user by the transmission method.

REFERENCE SIGNS LIST 1 wearable device
2 control server
23 speaker
25 projection unit
61 controller
91 blower unit
92 thermal adjustment unit
93 vibration unit
94 robot arm unit
81 context information generation unit
82 transmission controller
111 controller
113 action information storage unit
121 context recognition unit
122 action determination unit
123 control signal generation unit

The invention claimed is:
1. An information processing system, comprising:
a storage configured to store a database; and
a processor configured to:
acquire context information representing at least one of a surrounding environment of a user associated with a device, a feeling of the user, a situation of the user, feelings of people around the user, or situations of the people;
recognize a context of the user based on the context information;
determine a first action and a second action as a plurality of actions corresponding to the context, wherein the first action and the second action are registered in the database in association with the context, and the first action is opposite to the second action;
determine respective transmission methods for transmission of the first action and the second action to the user, wherein the determined respective transmission methods are suitable for the context, the first action, and the second action; and
control a function of the device for the transmission of one of the first action or the second action by one of the determined respective transmission methods.

2. The information processing system according to claim 1, wherein the processor is further configured to transmit the first action and the second action corresponding to the context to the user by the determined respective transmission methods at separate timings.

3. The information processing system according to claim 1, wherein the processor is further configured to:
determine one of the first action or the second action as an action corresponding to the context;
determine a transmission method suitable for the context and the one of the first action or the second action; and
transmit the one of the first action or the second action to the user by the determined transmission method.

4. The information processing system according to claim 1, wherein the processor is further configured to:
predict a behavior of the user based on the acquired context information;
select one of the first action or the second action that is associated with the context, depending on a result of the predicted behavior of the user; and
determine a transmission method suitable for the context and the selection.

5. The information processing system according to claim 1, further comprising a communication unit configured to receive the context information transmitted from the device, wherein
the processor is further configured to control the communication unit to send a control signal to the device,
the control signal indicates that the first action and the second action corresponding to the context are to be transmitted to the user by the respective transmission methods.

6. The information processing system according to claim 1, wherein the processor is further configured to:
analyze content of a message to the user; and
recognize the context of the user depending on a result of the analysis.

7. The information processing system according to claim 1, wherein the respective transmission methods include at least one of a first method that uses wind, a second method that uses vibration, a third method that uses sound, or a fourth method that uses drive of a robot arm provided to the device.

8. The information processing system according to claim 7, wherein the first method generates the wind having a temperature corresponding to the one of the first action or the second action to be transmitted.

9. The information processing system according to claim 7, wherein the second method generates the vibration in a pattern corresponding to the one of the first action or the second action to be transmitted.

10. The information processing system according to claim 7, wherein the third method comprises output of the sound of a tone corresponding to the one of the first action or the second action to be transmitted.

11. The information processing system according to claim 7, wherein
the fourth method comprises the drive of the robot arm to pull hair of the user or push back the user, and
the device is wearable by the user.

12. The information processing system according to claim 1, wherein the device is wearable by being hooked on an ear, and at least a part of an ear hook portion in the device is made of a material configured to deform depending on a body temperature of the user.

13. The information processing system according to claim 1, wherein the device is wearable by being put on a shoulder of the user, and at least a part of a casing of the device is made of a flexible and deformable material.

14. A non-transitory computer-readable medium having stored thereon, computer-executable instructions which, when executed by a processor, cause the processor to execute operations, the operations comprising:
acquiring context information representing at least one of a surrounding environment of a user associated with a device, a feeling of the user, a situation of the user, feelings of people around the user, or situations of the people;
recognizing a context of the user based on the context information;
determining a first action and a second action as a plurality of actions corresponding to the context, wherein the first action and the second action are registered in a database in association with the context, and the first action is opposite to the second action;
determining respective transmission methods for transmission of the first action and the second action to the user, wherein the determined respective transmission methods are suitable for the context, the first action, and the second action; and
controlling a function of the device for the transmission of one of the first action or the second action by one of the determined respective transmission methods.

15. An information processing method, comprising:
acquiring context information representing at least one of a surrounding environment of a user associated with a device, a feeling of the user, a situation of the user, feelings of people around the user, or situations of the people;
recognizing a context of the user based on the context information;
determining a first action and a second action as a plurality of actions corresponding to the context, wherein the first action and the second action are registered in a database in association with the context, and the first action is opposite to the second action; and
determining respective transmission methods for transmission of the first action and the second action to the user, wherein the determined respective transmission methods are suitable for the context, the first action, and the second action; and
controlling a function of the device for the transmission of one of the first action or the second action by one of the determined respective transmission methods.

16. An information processing system, comprising:
a control server including:
a first communication unit configured to receive context information representing at least one of a surrounding environment of a user associated with a device, a feeling of the user, a situation of the user, feelings of people around the user, or situations of the people, wherein the context information is sent from the device; and
a first controller configured to:
recognize a context of the user based on the context information;
determine an action corresponding to the context;
determine a transmission method for transmission of the action to the user, wherein the transmission method is suitable for the context and the action; and
control the first communication unit to send a control signal to the device, wherein the control signal indicates that the action corresponding to the context is to be transmitted to the user by the transmission method; and
the device including:
a generation unit configured to generate the context information and transmit the context information to the control server;
a second communication unit configured to receive the control signal sent from the control server;
an output unit configured to transmit the action to the user; and
a second controller configured to control, according to the control signal, the output unit to transmit the action to the user by the transmission method.

17. The information processing system according to claim 1, wherein
the processor is further configured to control a parameter of the function of the device for the transmission of the first action and the second action by the determined respective transmission methods, wherein the parameter corresponds to the first action and the second action to be transmitted,
the function of the device comprises output of sound, and the parameter comprises a tone of the sound,
the function of the device comprises generation of a vibration, and the parameter comprises a pattern of the vibration, and
the function of the device comprises generation of wind, and the parameter comprises a temperature of the wind.

18. An information processing system, comprising:
a storage configured to store a database; and
a processor configured to:
acquire context information representing at least one of a surrounding environment of a user associated with a device, a feeling of the user, a situation of the user, feelings of people around the user, or situations of the people;
recognize a context of the user based on the context information;

determine a first action and a second action corresponding to the context, wherein the database comprises a plurality of actions including the first action and the second action registered in association with the context;

predict a behavior of the user based on the context information;

select one of the first action or the second action that is associated with the context, depending on a result of the predicted behavior of the user;

determine a transmission method suitable for the context and the selection, wherein the determined transmission method is suitable for the context and the selected one of the first action or the second action; and control a function of the device for transmission of the selected one of the first action or the second action by the determined transmission method.

\* \* \* \* \*